(12) United States Patent
Renzi et al.

(10) Patent No.: US 7,745,420 B2
(45) Date of Patent: Jun. 29, 2010

(54) METHODS FOR INCREASING IN VIVO EFFICACY OF OLIGONUCLEOTIDES AND INHIBITING INFLAMMATION IN MAMMALS

(75) Inventors: Paolo Renzi, Westmount (CA); Mustapha Allam, Montréal (CA); Zoulfia Allakhverdi, Montréal (CA)

(73) Assignee: Topigen Pharmaceutique, Inc., Montreal, Quebec (CA)

( * ) Notice: Subject to any disclaimer, the term of this patent is extended or adjusted under 35 U.S.C. 154(b) by 589 days.

(21) Appl. No.: 10/482,949

(22) PCT Filed: Jul. 8, 2002

(86) PCT No.: PCT/CA02/01046

§ 371 (c)(1), (2), (4) Date: Aug. 16, 2004

(87) PCT Pub. No.: WO03/004511

PCT Pub. Date: Jan. 16, 2003

(65) Prior Publication Data

US 2005/0032723 A1 Feb. 10, 2005

Related U.S. Application Data

(60) Provisional application No. 60/303,071, filed on Jul. 6, 2001.

(51) Int. Cl.
*A61K 31/70* (2006.01)
(52) U.S. Cl. .......................................... 514/46; 536/24.5
(58) Field of Classification Search .................. None
See application file for complete search history.

(56) References Cited

U.S. PATENT DOCUMENTS

| | | | |
|---|---|---|---|
| 3,337,530 A | | 8/1967 | Hanze |
| 5,523,205 A | * | 6/1996 | Cossart et al. ................. 435/6 |
| 5,856,466 A | | 1/1999 | Guinosso et al. |
| 5,925,624 A | | 7/1999 | Gregson et al. |
| 6,175,004 B1 | | 1/2001 | Ross et al. |

FOREIGN PATENT DOCUMENTS

| | | | |
|---|---|---|---|
| WO | WO 99/02732 | | 1/1999 |
| WO | WO 99/66037 | * | 12/1999 |
| WO | WO 99 66037 A | | 12/1999 |
| WO | WO 99 67378 A | | 12/1999 |
| WO | WO 00/09525 | * | 2/2000 |
| WO | WO 00 12563 A | | 3/2000 |
| WO | WO 00/62736 | | 10/2000 |

OTHER PUBLICATIONS

Buhr et al (Nucl. Acids. Res. 24(15): 2974-2980, 1996).*
Le Moine et al (Journal of Immunology, 156(11): 4408-14, 1996).*
Marak et al (Opthalmic Res. 20(4): 220-226, 1988).*
Crooke S T: "Basic Principles of Antisense Therapeutics" Antisense Research and Applications, CRC Press, GB, 1998, pp. 1-50, XP000900999 p. 12, pp. 22-26, table 1, pp. 33-36.
Sanghvi Y S: "Heterocyclic Base Modifications in Nucleic Acids and Their Applications in Antisense Oligonucleotides" Antisense Research and Applications, CRC Press, GB, 1993, pp. 273-288, XP002921486 pp. 274 (introduction), p. 280, figure 3, compounds 34, 39, 41, 49a.
Uhlmann E et al: "Antisense Oligonucleotides a New Therapeutic Principle" Chemical Reviews, American Chemical Society. Easton, US, vol. 90, No. 4, Jun. 1, 1990, pp. 543-584, XP000141412 ISSN 0009-2665 pp. 556-557, figure 33, pp. 573-574.
Balow G et al: "Biophysical and antisense properties of oligodeoxynucleotides containing 7-propenyl-, 7-iodo- and 7-cyano-7-deaza-2-amino-2'deoxya denosines" Nucleic Acids Research, Oxford University Press, Surrey, GB, vol. 26, No. 14, 1998, pp. 3350-3357, XP002157793 ISSN: 0305-1048 p. 3355 last paragraph, p. 3356 first paragraph.
A.R. Hanze: "Nucleic acids. V. Nucleotide Derivatives of Tubercidin (7-Deazaadenosine)" Biochemistry, vol. 7, No. 3, 1968; pp. 932-939, XP002224917 Compounds XII and XIII, Figure 2; p. 934.
J. Santalucia, R. Kierzek, D.H. Turner: "Functional Group Substitutions as Probes of Hydrogen Bonding between GA Mismatches in RNA Internal Loops" Journal of the American Chemical Society, vol. 113, 1991, pp. 4313-4322, XP002224918 p. 4314, 2A mismatch, Tables, examples.
R. Saladino, E. Mincione, C. Crestini, N. Mezzetti: "Transformations of thiopyrimidine and thiopurine nucleosides following oxidation with dimethyldioxirane" Tetrahedron, vol. 52, No. 19, 1996, pp. 6759-6780, XP002224919 compound 24b p. 6765-p. 6767.
Nandanan E. el al: "Structure-activity relationships of bisphosphate nucleotide derivatives as P2Y1 receptor antagonists and partial agonists" Journal of Medicinal Chemistry, vol. 42, 1999, pp. 1625-1638, XP002224920 p. 1627, compounds 29a and 29b.

(Continued)

Primary Examiner—Richard Schnizer
(74) Attorney, Agent, or Firm—Nixon Peabody LLP; Jeffrey N. Townes

(57) ABSTRACT

The invention relates to the use of nucleotide substitutes for increasing the in vivo efficacy of nucleic acid molecules and also for inhibiting inflammation in mammals. More particularly, the present invention relates to the use of 2'6'diaminopurine (DAP) and analogs thereof per se in anti-inflammatory compositions, and also for preparing nucleic acid molecules having an increased in vivo physiological efficiency and a reduced toxicity as compared to conventional oligos. The invention is particularly useful for the preparation of antisense oligonucleotides for treating pulmonary/respiratory diseases such as cystic fibrosis, asthma, chronic bronchitis, chronic obstructive lung disease, eosinophilic bronchitis, allergies, allergic rhinitis, pulmonary fibrosis, adult respiratory distress syndrome, sinusitis, respiratory syncytial virus or other viral respiratory tract infection and cancer.

10 Claims, 15 Drawing Sheets

OTHER PUBLICATIONS

S. Ali el al: "Absorption, distribution, metabolism and excretion of a respirable antisense oligonucleotide for asthma" American Journal of Respiratory and Critical Care Medicine, vol. 163, 2001, pp. 989-993, XP002224921 cited in the application, the whole document.

Ortoleva-Donnelly, Lori et al., RNA; 4:498-519 (1998).

Strauss-Soukup, Juliane K. et al.; J. Mol. Biol. 302:339-358 (2000).

Strobel, Scott A. et al.; Proc. Natl. Acad. Sci. USA; 94:2903-2908 (Apr. 1997).

Crooke, S.T., "Progress in Antisense Therapeutics", Hematologic Pathology, 9(2), 59-72 (1995).

Cheng, X., "Structure and Function of DNA Methyltransferases", Annu. Rev. Biophys. Biomol. Struct., 24:293-318, (1995).

Khudyakov, I. Ya., et al., "Cyanophage S-2L Contains DNA With 2,6-Diaminopurine Substituted for Adenine", Virology 88, 8-18 (1978).

Balzarini, Jan, et al., "The 2',3'-Dideoxyriboside of 2,6-Diaminopurine Selectively Inhibits Human Immunodeficiency Virus (HIV) Replication in Vitro ", Biochemical and Biophysical Research Communications, vol. 145, No. 1, pp. 269-276, (1987).

Rackwitz, H.R. et al., "The Stereochemical Basis of Template Function", Eur. J. Biochem, 72, 191-200, (1977).

Templin, M.V. et al., "Pharmacokinetic and Toxicity Profile of a Phosphorothioate Oligonucleotide Following Inhalation Delivery to Lung in Mice", Antisense and Nucleic Acid Drug Development 10:359-368, (2000).

Ali, S. et al., "Absorption, Distribution, Metabolism, and Excretion of a Respirable Antisense Oligonucleotide for Asthma", American Journal Respir Crit Care Med, vol. 163, pp. 989-993, (2001).

Chollett, A. et al., "DNA containing the base analogue 2-aminoadenine: preparation, use as hybridization probes and cleavage by restriction endonucleases", Nucleic Acids Research, vol. 16, No. 1, pp. 305-317 (1988).

Bailly, C. et al., "Transferring the purine 2-amino group from guanines to adenines in DNA changes the sequence-specific binding of antibiotics", Nucleic Acids Research, vol. 23, No. 6, pp. 885-892, (1995).

Bailly, C. et al., "PCR-based development of DNA substrates containing modified bases: An efficient system for investigating the role of the exocyclic groups in chemical and structural recognition by minor groove binding drugs and proteins", Proc. Natl. Acad. Sci. USA, vol. 93, pp. 13623-13628, Nov. 1996.

Hoheisel, J.D. et al., "Quantitative measurements on the duplex stability of 2,6-diaminopurine and 5-chloro-uracil nucleotides using enzymatically synthesized oligomers", Federation of European Biochemical Societies, vol. 274, No. 1,2, pp. 103-106, Nov. 1990.

Renzi, P.M. et al., "Effect of Interleukin-2 on the Airway Response to Antigen in the Rat [1-4]", Am Rev Respir Dis 146:163-169, (1992).

Mann, J.S. et al., "Airway effects of purine nucleosides and nucleotides and release with bronchial provocation in asthma", J. Appl. Physiol. 61:1667-1676, (1986).

Tanaka, M. et al., "Respirable antisense oligonucleotides: a new drug class for respiratory disease", Respiratory Research 2:5-9, (2001).

Dias, N. et al., "Antisense Oligonucleotides: Basic Concepts and Mechanisms", Molecular Cancer Therapeutics, vol. 1, pp. 347-355, Mar. 2002.

Gauvreau, G.M. et al., "Antisense Therapy against CCR3 and the Common Beta Chain Attenuates Allergen-induced Eosinophilic Responses", Am J Respir Crit Care Med, vol. 177, pp. 952-958, (2008).

* cited by examiner

7-Deaza-2'-deoxyadenosine 2,6-Diaminopurine-2'-deoxyriboside
(2-Amino-2'-deoxyadenosine)

"DAP"

2-amino-9-(B-D-2'-deoxyribofuranosyl) purine

Adenine

N⁶-Methyl-2'deoxyadenosine

2-Aminoadenosine
(2,6-diaminopurine riboside)

Inosine (Hypoxanthine 9-β-D-ribofuranoside)

Adenosine (Adenine-9-β-D-ribofuranoside)

METHODS FOR INCREASING IN VIVO EFFICACY OF OLIGONUCLEOTIDES AND INHIBITING INFLAMMATION IN MAMMALS

CROSS-REFERENCE TO RELATED APPLICATIONS

This application is a 371 National Phase Entry Application of co-pending International Application PCT/CA02/01046 filed on 8 Jul. 2002 which designated the U.S and which claims the benefit of U.S. Provisional Application 60/303,071 filed 6 Jul. 2001.

BACKGROUND OF THE INVENTION (a) Field of the Invention

The invention relates to the use of nucleotide substitutes for increasing the in vivo efficacy of nucleic acid molecules and also for inhibiting inflammation in mammals.

More particularly, the present invention relates to the use of 2'6'diaminopurine (DAP) and analogs thereof per se in anti-inflammatory compositions, and also for preparing nucleic acid molecules having an increased in vivo physiological efficiency and a reduced toxicity.

(b) Brief Description of the Prior Art

Therapeutic approaches based on the use of nucleic acid molecules are becoming more and more popular. Gene-based therapies and antisense based-therapies will probably change radically medicine in a near future.

The problems to date with nucleic acid molecules as therapeutics, and more particularly with antisense oligonucleotides, have been toxicity (both systemic and topical), stability, and non-specific binding to cell surface proteins. The toxicity of antisense oligonucleotides seems to vary between species, rats being the most sensitive, although the toxicity appears at doses higher than those that are therapeutically effective (see S T Crooke, *Hematologic Pathology*, 1995, 9:5972 for a review). In pulmonary/respiratory diseases, nucleic acid molecules toxicity associated with the administration of therapeutic antisenses/genes include: an increase in immune stimulation, a mononuclear cellular-inflammatory infiltrate into the lungs, and possibly hypersensitivity and bronchoconstriction of the airways.

Several solutions that are less than optimum have been proposed up to date for circumventing the toxicity problem. Among the most popular there is the preparation of nucleic acid molecules containing various modified DNA bases, RNA bases, and/or a modified backbone structure. For instance, WO 99/67378 describes antisense oligonucleotides constructs based on modified sugars. Also, Nyce has postulated, although not demonstrated, in WO 00/09525 and WO 00/62736 that the adenosine base included in antisense oligonucleotides for treating respiratory diseases is a major cause of toxicity in lungs. Accordingly, Nyce proposes low adenosine oligonucleotides and oligonucleotides wherein the adenosine base has been replaced by an analog of adenosine. However, none of the low adenosine oligonucleotides and none of the adenosine analogs proposed by Nyce have ever been tested for their biological activity or their allegedly reduced toxicity.

2',6'-diaminopurine nucleoside (2-amino-2'-deoxyadenosine; DAP) was found to be present in DNA in place of adenosine by the cyanophage S-2L (Cheng, X., *Annu Rev Biophys Biomol Struct* 24: 293-318, 1995); Khudyakov, I. Y., et al., *Virology* 88: 8-18, 1978). Since then, 2',6'-diaminopurine nucleoside (DAP) has been widely used and studied, notably as a chemical starting point for the synthesis of antiviral compounds such as 2-amino-2',3'-dideoxyadenosine (not DAP) which is capable of selectively inhibiting human immunodeficiency virus (HIV) replication in vitro (Balzarini, J. et al., *Biochem. & Biophys. Res. Communications* 145:269-76 (1987). The use of DAP in antisense oligonucleotides or in gene therapy methods has however never been suggested.

Also, U.S. Pat. No. 5,925,624 and No. 5,889,178 describe derivatives of 2,6-diaminopurine-beta-D-ribofuranuronamide. Although these derivatives have an anti-inflammatory effect (mostly against neutrophil superoxide release) and that they could be used in the therapy of respiratory disease, they have a chemical formula which is different from the formula of DAP and analogs thereof.

In summary, there has been up to date no suggestion nor any evidence that DAP per se could be used in anti-inflammatory compositions, nor any suggestion or example that DAP and analogs thereof could be incorporated in nucleic acid molecules (gene constructs and antisenses) for increasing the in vivo efficacy of these oligos.

There is thus a need for more effective anti-inflammatory compositions comprising 2'6-diaminopurine and/or analogs thereof.

There is also a long felt need for nucleic acid molecules that would remain stable in the body while exhibiting high effectiveness and low toxicity.

There is more particularly a need for nucleic acid molecules incorporating a nucleotide substitute such as 2'6'diaminopurine (DAP) and analogs thereof, a need for composition comprising the same and a need for methods of using these nucleic acid molecules, particularly in gene and antisense therapies methods. No one has ever tested whether replacement of base(s) by a nucleotide substitute could affect the stability, binding, degradation efficacy and toxicity of antisense oligonucleotides, nor have they tested such modified antisense oligonucleotides for biological activity in cells, in culture or in animals.

The present invention fulfils these needs and also other needs which will be apparent to those skilled in the art upon reading the following specification.

SUMMARY OF THE INVENTION

An object of the invention is to provide nucleic acid molecules such as gene constructs and antisense oligonucleotides that would remain stable in the body while exhibiting high effectiveness and low toxicity.

According to an aspect of the invention, it is provided a method for increasing in vivo efficacy of an nucleic acid molecule that is administered to a mammal, comprising incorporating into the nucleic acid molecule at least one nucleotide substitute. Such an incorporation increases in vivo physiological effectiveness of the nucleic acid molecule and also reduces its toxicity when administered to a mammal, as compared to an nucleic acid molecule not incorporating the nucleotide substitute. According to a preferred embodiment, the nucleotide substitute is incorporated into the nucleic acid molecule for substituting therein an adenosine base. More preferably, the nucleotide substitute is selected from the group consisting of 2'6'-diaminopurine and analogs thereof. Preferred 2'6'-diaminopurine analogs include 2,6-diaminopurine hemisulfate, 2-amino-9-(B-D-2'-deoxyribofuranosyl) purine, 7-Deaza-2'-deoxyadenosine, N6-methyl-2'-deoxyadenosine, 2-aminoadenosine/2,6-diaminopurine riboside, salts thereof and functional derivatives thereof.

The invention also relates to an improved method for the in vivo administration of at least one nucleic acid molecule to a mammal subject. The improvement consists of incorporating into the nucleic acid molecule at least one 2'6'-diaminopurine and/or an analog thereof. Preferably, 2'6'-diaminopurine or its analog is incorporated into the nucleic acid molecule for substituting therein an adenosine base.

According to another aspect of the invention, it is provided an isolated or purified nucleic acid molecule selected from antisense oligonucleotides and nucleic acid molecules comprising a sequence coding for a therapeutic gene product, the nucleic acid molecule according to the present invention comprising a nucleotide substitute selected from the group consisting of 2'6'-diaminopurine and analogs thereof.

According to another aspect of the invention, it is provided a pharmaceutical composition comprising at least one nucleic acid molecule as defined previously and a pharmaceutically acceptable carrier. The composition of the invention may be useful for treating and/or preventing a disease selected from respiratory system diseases, neurological diseases, cardiovascular diseases, rheumatological diseases, digestive diseases, cutaneous diseases, ophtalmological diseases, urinary system diseases, cancers, pathogen infections, and genetic diseases, hypereosinophilia, general inflammation, and cancers.

According to a further aspect of the invention, it is provided a method of antisense therapy, comprising the step of administering, directly to the respiratory system of a mammal in need thereof, an effective therapeutic or prophylactic amount of at least one antisense oligonucleotide as defined previously. This method is useful for preventing and/or treating respiratory system diseases, cancers, pathogen infections, and genetic diseases, and more particularly respiratory system diseases associated with an inflammation of the lungs, the airways and/or the nose such as pulmonary fibrosis, adult respiratory distress syndrome, cystic fibrosis, chronic obstructive lung disease, chronic bronchitis, eosinophilic bronchitis, asthma, allergy, sinusitis, respiratory syncytial virus or other viral respiratory tract infection and hypereosinophilia.

According to another aspect of the invention, it is provided a method for inhibiting inflammation in a mammal, comprising the use of a nucleotide substitute selected from the group consisting of 2'6'-diaminopurine and analogs thereof. Typically, 2'6'diaminopurine or its analogue(s) are administered to the mammal. Preferably 2'6'-diaminopurine and its analogs are used as such in an anti-inflammatory composition, but they may be also incorporated into nucleic acid molecules. In a related aspect, the invention concerns an anti-inflammatory composition comprising: an adenosine antagonist compound selected from the group consisting of 2'6'-diaminopurine and analogs thereof; and a pharmaceutically acceptable carrier. Another related aspect concerns the use of 2'6'-diaminopurine and/or an analog thereof for the preparation of an anti-inflammatory composition.

DETAILED DESCRIPTION OF THE INVENTION

Figure 1A:
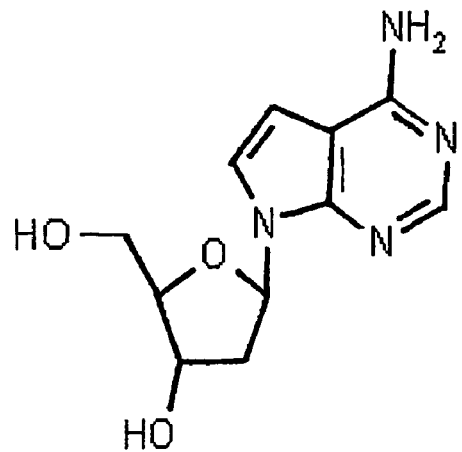
FIGS. 1A, 1B, 1C, and 1D shows the chemical structures of adenine, adenosine, inosine, 2'6'-diaminopurine (2-amino-2'-deoxyadenosine; DAP) and different analogs of DAP.
Figure 1A:
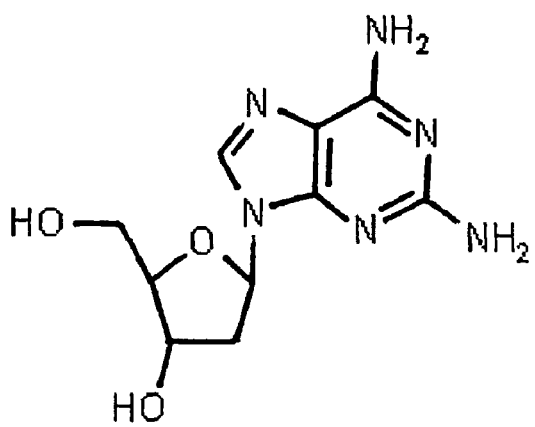
Figure 1B:
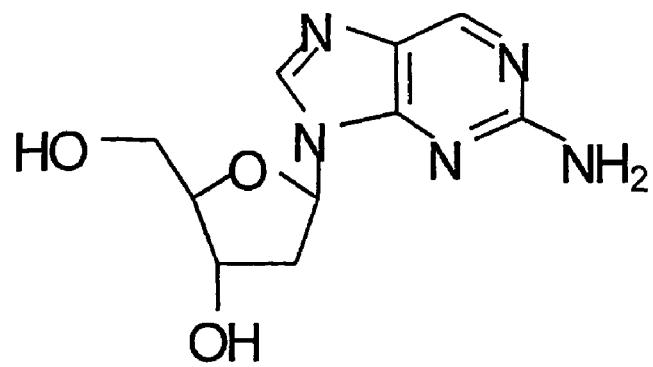
Figure 1B:
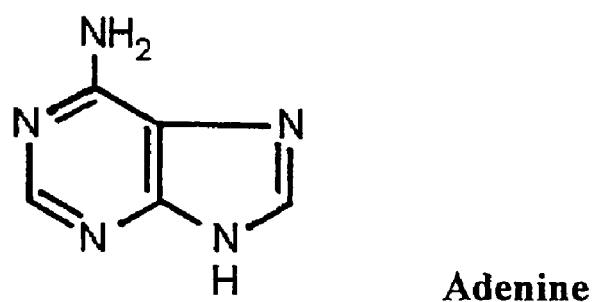
Figure 1C:
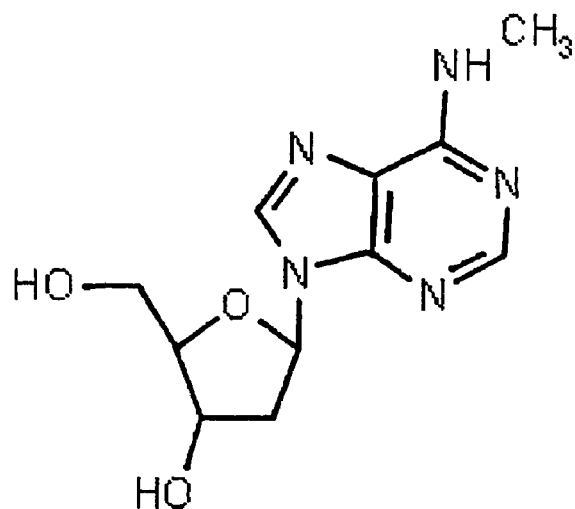
Figure 1C:
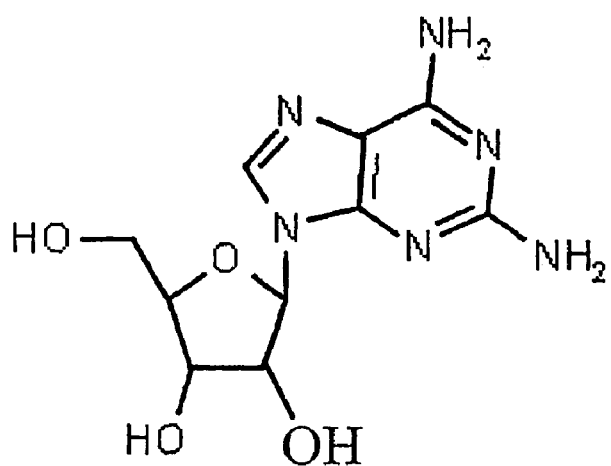
Figure 1D:
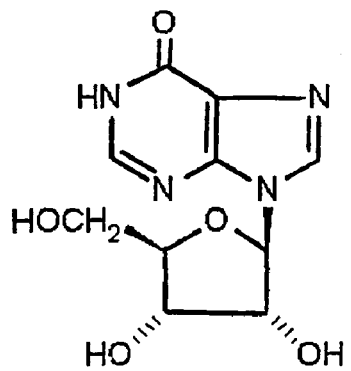
Figure 1D:
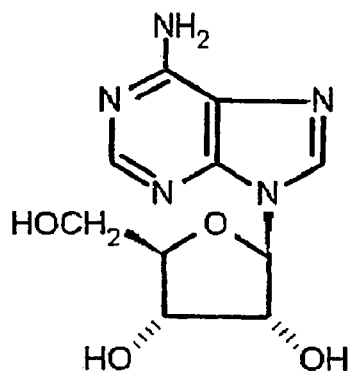

The present invention relates to nucleic acid molecules such as gene constructs and antisenses that would remain stable in the body while exhibiting high effectiveness and low toxicity. It also relates to the use of 2'6'-diaminopurine and analogs for inhibiting inflammation.

According to an aspect of the invention, there is provided a method for increasing in vivo efficacy of an nucleic acid molecule that is administered to a mammal. This method comprises the step of incorporating into the nucleic acid molecule at least one nucleotide substitute. As it will be shown in the examples herein after, such an incorporation increases the in vivo physiological effectiveness of the nucleic acid molecules and also reduces the toxicity of the nucleic acid molecules when administered to a mammal, as compared to nucleic acid molecules not incorporating the nucleotide substitute.

The "reduced toxicity" of the nucleic acid molecules may be evaluated using principles known in the art. According to a preferred embodiment of the invention, the nucleotide substitute is selected so that nucleic acid molecules incorporating the nucleotide substitute exhibit lower in vivo inflammatory properties, and thereby have a reduced toxicity. More preferably, the nucleotide substitute is selected so that the nucleic acid molecules incorporating this modification are capable of inhibiting recruitment of lymphocytes, eosinophils, macrophages and/or neutrophils at a site where these nucleic acid molecules are administered and/or at a site of disease.

According to a preferred embodiment of the invention, the nucleotide substitute is incorporated into the nucleic acid molecule for substituting therein an adenosine base. Preferably, the nucleotide substitute is 2'6'-diaminopurine (see FIG. 1) or an analog thereof. As used herein, "analogs of 2'6'-diaminopurine" include all compounds having a similar structure and substantially the same biological activity/efficacy of 2'6'-diaminopurine. Preferred 2'6'-diaminopurine analogs are also shown in FIG. 1 and include: 2,6-diaminopurine hemisulfate (1H-purine-2,6-diamine, sulfate (2:1); CAS 69369-16-0), 2-amino-9-(B-D-2'-deoxyribofuranosyl) purine (CAS 3616-24-8), 7-Deaza-2'-deoxyadenosine (CAS 60129-59-1), N6-methyl-2'-deoxyadenosine (CAS 2002-35-9), 2-aminoadenosine/2,6-diaminopurine riboside (CAS 2096-10-08), and salts thereof.

Among the 2'6'-diaminopurine analogs are also included all functional derivatives of 2'6'-diaminopurine i.e. all compounds that possess a biological activity/efficacy that is substantially similar to the biological activity/efficacy of 2'6'-diaminopurine and/or of the analogs thereof which are shown in FIG. 1.

According to another aspect of the invention, it is provided an isolated or purified nucleic acid molecule comprising a nucleotide substitute selected from the group consisting of 2'6'-diaminopurine and analogs thereof as defined previously. The nucleic acid molecule of the invention may consists of an antisense oligonucleotide, a double stranded RNA (as RNAi) or an nucleic acid molecule comprising a sequence coding for a therapeutic gene product. Preferably, the nucleotide substitute is incorporated into the nucleic acid molecule for substituting therein an adenosine base.

As used herein, the expression "nucleic acid molecule" means any DNA, RNA sequence or molecule having one nucleotide or more, including nucleotide sequences encoding a complete gene. The term is intended to encompass all nucleic acids whether occurring naturally or non-naturally in a particular cell, tissue or organism. This includes DNA and fragments thereof, RNA and fragments thereof, cDNAs and fragments thereof, expressed sequence tags, artificial sequences including randomized artificial sequences.

The nucleic acid molecules of the invention are synthesized using methods well known in the art. They may be in the form of a DNA, or an RNA, and they may comprise one or a plurality of mononucleotide linking residue(s) such as methylphosphonate, phosphotriester, phosphorothioate, phosphodiester, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyimino), methyleneoxy (methylimino), and phosphoramidate residues.

DAP base and analogs thereof may be introduced chemically into DNA and RNA sequences using conventional phosphoramidite chemistry. Alternatively, DAP can be incorporated into DNA and RNA by enzymatic methods via the use of DAP triphosphate and polymerases as it is well known in the art. Interestingly, DAP-triphosphate acts as a true analog of ATP for DNA synthetic enzymes (Rackwitz, H. R., et al. *Eur J Biochem* 72: 191-200, 1977).

The nucleic acid molecules of the invention may also be linked to a "carrier" molecule such as amino acids, peptides, proteins, peptidomimetics, small chemicals, ligands, lipids, nucleic acids, or carbohydrate moieties.

The size of the nucleic acid molecules of the invention will vary depending on a desired use, the oligo having typically from 2 to about 10 000 nucleotides. More preferably, the size of antisense nucleic acid molecules will vary from about 10 to about 100 nucleotides whereas the size for nucleic acid molecules comprising a sequence coding for a therapeutic gene product would typically vary from about 100 to about 10 000 nucleotides.

The nucleic acid molecules of the invention may be useful for treating and/or preventing various diseases. Typical examples of diseases that could benefit from the present nucleic acid molecules include respiratory system diseases, neurological diseases, cardiovascular diseases, rheumatological diseases, digestive diseases, cutaneous diseases, ophtalmological diseases, urinary system diseases, cancers, pathogen infections, genetic diseases, hypereosinophilia, general inflammation, and cancers. Most preferred nucleic acid molecules include the oligonucleotides listed hereinafter in Table 1.

TABLE 1

Antisense oligonucleotides for treating or preventing atopic diseases and neoplastic cell proliferation

| Target | Sequence | | SEQ ID NO: |
|---|---|---|---|
| Antisense oligonucleotides inhibiting the common subunit of IL-4 and IL-13 human receptor | agaccttcat | gttcccagag | 1 |
| | gttcccagag | cttgccacct | 2 |
| | cctgcaagac | cttcatgtt | 3 |
| | cgcccacagc | ccgcagagcc | 4 |
| | ctccatgcag | cctctcgcct | 5 |
| | ccgccggcgc | agagcagcag | 6 |
| | cgcccccgcc | cccgcccccg | 7 |
| Antisense oligonucleotides inhibiting the common subunit of IL-3, IL-5 and GM-CSF human receptor | gggtctgcag | cgggatggt | 8 |
| | ggtctgcagc | gggatggtt | 9 |
| | agggtctgca | gcgggatgg | 10 |
| | gcagggtctg | cagcgggat | 11 |
| | gcagcgggat | ggtttcttc | 12 |
| | cagcgggatg | gtttcttct | 13 |
| | gtctgcagcg | ggatggttt | 14 |
| Antisense oligonucleotides inhibiting the CCR3 human receptor | ctgggccatc | agtgctctg | 15 |
| | ccctgacata | gtggatc | 16 |
| | tagcatggcactgggc | | 17 |
| | ggagccagtcctagcgagc | | 18 |

Since the DAP-substituted nucleic acid molecules of the invention have an improved efficacy and/or a reduced toxicity, they could be used in gene therapy and DNA vaccination methods. For instance, DAP-substituted nucleic acid molecules could be used as therapeutics for inhibiting the multiplication of pathogens of the respiratory system; as a therapeutic or vaccine to treat or to prevent neoplastic cell proliferation in the lungs/airways/nose; as therapeutics or vaccines to treat genetic diseases of the lungs/airways/nose, such as cystic fibrosis; and as therapeutics or vaccines for the treatment and/or prevention of asthma, allergy, chronic obstructive lung disease, pulmonary fibrosis, chronic cough and mucus production, the adult respiratory distress syndrome, general inflammation, inflammatory diseases, cancer, pathogen infections (e.g. sinusitis, respiratory syncytial virus or other viral respiratory tract infection) genetic diseases, or any diseases of the respiratory system. In addition DAP and its analogs may be inserted into genes in place of adenine or any other base, or be administered in association with the genes (e.g. incorporated into a coding or non coding region) in order to decrease the immune response that occurs during gene therapy and/or improve the efficacy of gene therapy methods.

More particularly, DAP-substituted nucleic acid molecules could be used to treat pathogen infections and/or prevent them from occurring, by inhibiting replication of respiratory pathogens such as respiratory syncytial virus (RSV), rhinovirus, influenza virus, bacteria and other agents that cause diseases. Similarly, DAP-substituted nucleic acid molecules that have anti-tumor activity could be used for the treatment and prevention of lung or other cancers. DAP-substituted DNA or genes would also be particularly useful for therapeutic applications where an inflammatory response to the gene is not desired such as in the treatment of genetic diseases of the respiratory tract (e.g. cystic fibrosis).

Depending on a desired use, it may be necessary that the DAP-nucleic acid molecule be incorporated into a vector, such as a plasmid or a virus, and that it comprises a sequence coding for a therapeutic gene product.

According to a preferred embodiment of the invention, the nucleic acid molecules are antisense oligonucleotides. As it will be shown in the examples hereinafter, DAP-substituted antisense oligonucleotides, have an improved efficacy and/or a reduced toxicity. These antisenses could thus be used as therapeutic or vaccine directed against at least one lung/airway/nose mediator or receptor, as therapeutic for inhibiting the inflammatory reaction that is present in asthma or allergic rhinitis, and as therapeutic for preventing the development of allergy or asthma, or for desensitizing patients with these diseases.

For instance, DAP-substituted antisense oligonucleotides could be directed against nucleic acid sequences coding for mediators and receptors, or other components of the inflammation process, so that by inhibiting the expression of these proteins, the inflammatory process could be turned off in the lungs/airways (asthma, chronic obstructive lung disease therapeutic) or in the nose (allergic rhinitis), or in the sinuses (chronic sinusitis).

Therefore, a further aspect of the invention relates to a method of antisense therapy, the method comprising the step of administering to a mammal in need thereof, an effective therapeutic or prophylactic amount of at least one antisense oligonucleotide as defined previously. This method is particularly useful for preventing and/or treating respiratory system diseases, neurological diseases, cardiovascular diseases, rheumatological diseases, digestive diseases, cutaneous diseases, ophtalmological diseases, urinary system diseases, cancers, pathogen infections, genetic diseases, general inflammation and cancer.

According to a preferred embodiment, the antisense oligonucleotide is administered, directly to the respiratory system for preventing and/or treating a respiratory system disease associated with an inflammation of the lungs, the airways and/or the nose such as pulmonary fibrosis, adult respiratory distress syndrome, cystic fibrosis, chronic obstructive lung disease, chronic bronchitis, eosinophilic bronchitis, asthma, allergy, allergic rhinitis, sinusitis and hypereosinophilia.

Preferably, the nucleic acid molecules of the invention would be incorporated in a pharmaceutical composition comprising at least one of the nucleic acid molecules defined previously, and a pharmaceutically acceptable carrier.

The amount of nucleic acid molecules present in the composition of the present invention is a therapeutically effective amount. A therapeutically effective amount of nucleic acid molecules is that amount necessary so that the nucleic acid molecule perform its biological function without causing, into the host to which the composition is administered, overly negative effects. The exact amount of nucleic acid molecules to be used and composition to be administered will vary according to factors such as the oligo biological activity, the type of condition being treated, the mode of administration, as well as the other ingredients in the composition. Typically, the composition will be composed from about 1% to about 90% of nucleic acid molecule(s), and about 20 μg to about 20 mg of nucleic acid molecule will be administered.

The pharmaceutically acceptable carrier of the composition may be selected from the group consisting of solid carriers, liquid carriers and gas phase carriers. Advantageously, the carrier is selected from the group consisting of lipid particles, lipid vesicles, microcrystals and surfactants.

Further agents can be added to the composition of the invention. For instance, the composition of the invention may also comprise agents such as drugs, antioxidants, surfactants, flavoring agents, volatile oils, buffering agents, dispersants, propellants, and preservatives. For preparing such pharmaceutical compositions, methods well known in the art may be used.

The nucleic acid molecules and the composition of the invention may be given via various routes of administration. For instance, the composition may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously by injection or by infusion. The nucleic acid molecules and the composition of the invention may also be formulated as creams or ointments for topical administration. They may also be administered into the airways of a subject by way of a pressurized aerosol dispenser, a nasal sprayer, a nebulizer, a metered dose inhaler, a dry powder inhaler, or a capsule. Suitable dosages will vary, depending upon factors such as the amount of each of the components in the composition, the desired effect (fast or long term), the disease or disorder to be treated, the route of administration and the age and weight of the individual to be treated. Anyhow, for administering the nucleic acid molecules and the composition of the invention, methods well known in the art may be used.

As mentioned previously, the present invention also relates to the use of 2'6'-diaminopurine and analogs thereof for inhibiting inflammation in a mammal. Therefore, the invention also provides an anti-inflammatory composition comprising: 2'6'-diaminopurine and/or an analog thereof; and a pharmaceutically acceptable carrier. The invention also provides a method for inhibiting inflammation in a mammal, comprising the use as such of 2'6'-diaminopurine and analogs thereof and/or the use of this (these) compound(s) in pharmaceutical compositions. 2'6'-diaminopurine and analogs thereof may be administered as such or incorporated linked to a "carrier" molecule such as amino acids, peptides, proteins, peptidomimetics, small chemicals, ligands, lipids, nucleic acids, or carbohydrate moieties. In a preferred embodiment, 2'6'-diaminopurine and/or its analogs are incorporated into a nucleic acid molecule such that degradation of the nucleic acid molecule by the body results in the liberation of 2'6'-diaminopurine and/or its analogs.

In a related aspect, the invention concerns an anti-inflammatory composition comprising an adenosine antagonist compound selected from the group consisting of 2'6'-diaminopurine and analogs thereof; and a pharmaceutically acceptable carrier. Another related aspect concerns the use of 2'6'-diaminopurine and/or an analog thereof for the preparation of an anti-inflammatory composition.

The anti-inflammatory composition of the invention could be particularly useful for the prevention and/or treatment of any disease (topical or systemic) where activation of an adenosine receptor is substantially toxic, and more particularly, systemic, organ- or tissues-specific inflammation. More particularly, the anti-inflammatory composition of the invention could be particularly useful for the prevention and/or treatment of any inflammation that is associated with and/or caused by a cancer, a respiratory system disease, a neurological disease, a cardiovascular disease, a rheumatological disease, a digestive disease, a cutaneous disease, an ophtalmological disease and a urinary system disease. More particular examples of respiratory system diseases that could benefit from the anti-inflammatory composition of the invention include pulmonary fibrosis, adult respiratory distress syndrome, cystic fibrosis, chronic obstructive lung disease, chronic bronchitis, eosinophilic bronchitis, asthma, allergy, and hypereosinophilia.

As described hereinbefore, the amount of 2'6'-diaminopurine and analogs thereof to be used in the composition of the invention, the amount of the composition to be administered and its routes of administration will vary according to various factors well known in the art.

As it will now be demonstrated by way of examples hereinafter: (1) the present invention provides a novel antisense technology, based on analogs of 2,6 diaminopurine, substituted for adenosine; (2) not all substitutes of adenosine are equally effective, DAP and its analogs being surprisingly more effective than others; (3) the nucleic acid molecules of the invention are equally and surprisingly even more effective at inhibiting the synthesis of target proteins than standard antisense oligonucleotides; (4) that the DAP-based antisense technology according to the present invention is more powerful and constitutes a significant advance over existing technologies since DAP-based antisenses have more significant anti-inflammatory effects than conventional antisense oligonucleotides; (5) DAP-nucleic acid molecules seem to exert their anti-inflammatory effects by a mechanism that does not seem to be related to inhibition of adenosine receptors; (6) the present nucleic acid molecules have significantly reduced toxicity for any inflammatory disease and/or the lungs/airways; (7) the use of the DAP-nucleic acid molecules, compositions and methods of the invention would be more effective than using regular antisenses (containing no DAP); and (8) finally, 2'6'-diaminopurine per se and its analogs have anti-inflammatory activities.

EXAMPLES

The following examples are illustrative of the wide range of applicability of the present invention and are not intended to limit its scope. Modifications and variations can be made therein without departing from the spirit and scope of the invention. Although any method and material similar or equivalent to those described herein can be used in the practice for testing of the present invention, the preferred methods and materials are described.

A) INTRODUCTION

Antisense oligonucleotides (AS) are a new class of pharmaceuticals that have been extensively described in the scientific and patent literature. This therapeutic strategy could potentially be applied to any disease where an over-expression of one or several genes is believed to cause the presence or persistence of the disease. An increased efficacy and anti-inflammatory efficacy would make AS an important therapeutic strategy for every respiratory disease including asthma, bronchiolitis, viral and other forms of infection, rhinitis, cystic fibrosis, chronic bronchitis, chronic obstructive lung disease, eosinophilic and other forms of cough, pulmonary fibrosis, adult respiratory distress syndrome, conjunctivitis and other forms of eye or skin inflammatory diseases.

A review of the systemic effects and toxicity of antisense oligonucleotides has been summarized by S T Crooke (*Hematologic Pathology*, 9: 5972; 1995). One way to circumvent the toxicity of the PS oligonucleotides would be to administer them to the site of the disease that they are designed to treat, minimizing systemic distribution and thus the toxicity associated with it. PS AS oligonucleotides have been nebulized to the lungs of mice or rabbits (Templin M V et al. *Antisense and nucleic acid drug development*, 10:359-368; 2000; Ali S et al. *Am J Respir Critic Care Med* 163:989-993; 2001). Results have shown that there is very little systemic distribution at doses that would be considered therapeutically effective. However, at higher doses a multifocal cellular infiltrate occurs in the lungs of mice, comprising primarily lymphocytes and neutrophils, with a few macrophages and monocytes. Although the adenosine base included in oligonucleotides may have pro or anti-inflammatory effects, we have previously reported in patent WO 99/66037 that an antisense oligonucleotide directed against the CCR3 receptor and containing 5 adenosines per 18 mer (27.7% adenosine) was effective at inhibiting the asthmatic response in vivo in rats.

No one has systematically tested whether replacement of bases by analogs could affect the stability, binding, degradation efficacy and toxicity of antisense oligonucleotides, nor have they tested them for biological activity in cells in culture or in animals. 2,6 diaminopurine (DAP) was found to be present in DNA in place of adenosine by the cyanophage S-2L (Cheng, X., *Annu Rev Biophys Biomol Struct* 24: 293-318, 1995); Khudyakov, I.Y., et al., *Virology* 88: 8-18, 1978). DAP alters the structure of duplex DNA and introduces a third hydrogen bond in the D:T duplex (similar to the three hydrogen bonds formed by cytosine and guanosine) when compared with A:T duplex (Chollett, A. and Kawashima, E. of Biogen SA (Geneva), *Nucleic Acids Research* 16:305-17, 1988). This extra hydrogen bond leads to increase selectivity and hybridization strength during DNA-DNA hybridization, as well as the inhibition of cleavage of several restriction enzymes (Bailly, C. and Waring, M. J., *Nucleic Acids Research* 23:885-92, 1995; Bailly, C. *PNAS* 93: 13623-8, 1996).

The additional N2 amino group of the C2 carbon in DAP is used for base pairing. The additional bond causes increased DNA duplex stability and renders the minor groove of both B- and Z-DNA more hydrophilic. DAP substitution for adenosine causes an increase in the $T_m$ of DAP containing DNA, the temperature at which two duplexed complementary DNA strands melt, of 1.5° C. per DAP residue (Hoheisel, J. D., Lehrach, H., *FEBS Letters* 274:103-6, 1990). DAP and its analogs have thus the potential to increase the efficacy and anti-inflammatory activity of AS oligonucleotides when included within the oligonucleotide either as substitution for a base, in addition to the bases, when incorporated to gene therapy or as seen below, when administered alone.

B) MATERIAL AND METHODS

Experiments with Cell Lines

Experiments were performed to assess whether antisense oligonucleotides described in international application WO 99/66037 (incorporated herein) directed against the common beta sub-unit of the IL-3, IL-5 and GM-CSF receptor, could inhibit the expression and the function of this receptor when modified by replacing adenosine by either 2-amino-2'-deoxyadenosine or inosine. TF-1 and U937 cells express high levels of GM-CSF receptors. In addition, TF-1 cells are dependent on GM-CSF for survival. These cells were cultured in RPMI 1640 supplemented with 10% heat-inactivated fetal calf serum, penicillin, streptomycin and 1-glutamine at 37° C. in 5% CO2 (the TF-1 cells were supplemented with GM-CSF). For 12 hours they were either cultured in medium alone or medium with sense (107S: 5'-ACCAT CCCGCTGCA-GACCC-3' (SEQ ID NO:19) or antisense (107A: 5'-GGGTCTGCAGCGGGATGGT-3'; SEQ ID NO:20) oligonucleotides to the common beta sub-unit of the IL-3, IL-5 and GM-CSF receptor. The sequence for 107A-DAP was: 5'-GGGTCTGCDapGCGGGDapTGGT-3' (SEQ ID NO:21); the sequence for 107A-inosine (107A-I) was: 5'-GGGTCT-GCIGCGGGIT GGT-3' (SEQ ID NO:22). The cells were retrieved and washed 3 times. RNA was then retrieved and the presence of the beta chain of the receptor was assessed by semi-quantitative RT-PCR.

Animals

Brown Norway rats 6-8 weeks of age and weighing 220-275 g were obtained from Harlan-Sprague-Dawley (Walkerville, Md.). Rats were maintained in conventional animal facilities.

Sensitization to Ovalbumin

Active sensitization of rats was performed by subcutaneous injection of 1 ml of saline containing 1 mg of chicken egg ovalbumin (OA) (Sigma, St. Louis, Mo.) and 3.5 mg of aluminum hydroxide gel (BDH Chemicals, Poole, UK).

Ovalbumin Challenge

On day 14 after sensitization with ovalbumin, after general anesthesia with 65 mg/Kg pentothal and endotracheal intubation, ovalbumin challenge is performed by injecting 200 micrograms of ovalbumin in 60 μl intratracheally. After 8 hours or 15 hours, the rats are again intubated after general anesthesia and a lung lavage consisting of 5 times 5 ml instillation of 0.9% saline is performed. Cells are washed, counted and centrifuged onto slides in a Cytospin III™. A differential cell count is performed.

Measurement of Airway Responses

The equipment and methodology for measuring pulmonary resistance was as previously described (Renzi, P. M., et al. Am. Rev. Respir. Dis 146: 163-169, 1992). General anesthesia was induced with either pentothal (50 mg/kg) or urethane (1.1 g/kg) intra-peritoneally. Endo-tracheal intubation was then performed using a 6 cm length of PE-240™ polyethylene catheter. A heating pad was used to maintain constant body temperature and rectal temperature was monitored continuously with an electronic thermometer (Telethermometer™, Yellow Springs Instrument Co., Yellowsprings, Ohio). Lung resistance (RL) was measured during spontaneous tidal breathing with the animals in the lateral decubitus position. Flow was measured by placing the tip of the tracheal tube inside a small Plexiglass™ box (265 ml in volume). A Fleish™ No. 0 pneumotachograph coupled to a differential pressure transducer (MP-45+2 cm $H_2O$; Validyne Corp, Northridge, Calif.) was attached to the other end of the box to measure airflow, and volume was obtained by numerical integration of the flow signal. Changes in esophageal pressure were measured by using a saline-filled catheter and a differential pressure transducer (Sanborn 267 BC™; Hewlett Packard, Waltham, Mass.). The other port of the transducer was connected to the box. The esophageal catheter consisted of polyethylene tubing (PE-200™) 20-cm long attached to a shorter length (6 cm) of tubing (PE-100™). Transpulmonary pressure was computed as the difference between esophageal and box pressure. The airway response was evaluated from RL, which was determined by fitting the equation of motion of the lung by multiple linear regression using commercial software (RHT-Infodat Inc., Montreal, Quebec, Canada).

Measurement of Lung Resistance Immediately after Administration of Regular or Modified PS Antisense Oligonucleotides On day 14 after sensitization with ovalbumin, after general anesthesia with 65 mg/Kg pentothal and endotracheal intubation, 60 µg of an PS AS oligonucleotide directed against the rat common Beta chain of the GM-CSF, IL-3 and IL-5 receptor (AS141A: 5'-TGGCACTTTAGGTGGCTG-3'; SEQ ID NO:23) was injected intratracheally. Lung resistance was measured at baseline, every five minutes for 30 minutes and at 15 minutes intervals. The same experiments were repeated with modified AS141 where adenosine has been replaced by DAP, AS141-DAP (5'-TGGCDapCTTTDapGGTGGCTG-3'; SEQ ID NO:24) or by inosine, AS141-I (5'-TGGCICTT-TIGGTGGCTG-3; SEQ ID NO:25).

Experiments Assessing the Airway Responsiveness to Adenosine and DAP Nucleoside and Other Specific DAP Analogs On day 14 post-sensitization, rats were anesthetized with pentothal (65 mg/kg), intubated, and baseline RL was measured. Rats were given incremental doses intratracheally of adenosine (CAS 58-61-7), 2,6-diaminopurine hemisulfate salt (CAS 69369-16-0), DAP (2-amino-2-deoxyadenosine; CAS 4546-70-7), 2-amino-9-(B-D-2'-deoxyribo furanosyl) purine (CAS 3616-24-8), 7-Deaza-2'deoxyadenosine (CAS 60129-59-1), N6-Methyl-2'-deoxyadenosine (CAS 2002-35-9), 2-aminoadenosine/2,6-diamunopurine riboside (CAS 2096-10-08) over the dose range of 0.125 µg to 100 µg in 50 µl of either saline or saline plus acetic acid. Immediately after each dose RL was measured. DAP was dissolved as follows: 3 mg of DAP was combined with 100 µl of acetic acid, adjusted to 1.5 to 3 ml by the addition of saline, and heated to 70° C. This gave a final concentration of 1 to 2 µg/µl. Dilutions were performed in the same buffer. Control animals received saline with acetic acid at the same final concentration as indicated.

Experiments Assessing the Leukotriene D4 Responsiveness after Antigen Challenge

We have previously shown that the antisense ASA4 (5'-ACTCATATTC ATAGGGTG-3'; SEQ ID NO:26) directed against the rat CCR3 receptor was effective at inhibiting eosinophil influx into the lungs after antigen challenge (see WO 99/66037). We employed the same oligonucleotide sequences for these experiments. On day 14, the rats were intubated after general anesthesia with pentothal (65 mg/kg) and received 200 µg of ASA4, ASA4-DAP(5'-DapCTCDapT-DapTTCDapTDapGGGTG-3'; SEQ ID NO:27), mismatch ASA4-DAP (5'-CDapTCDapT TDapTCATGDapGGTG-3'; SEQ ID NO:28), AS141-DAP (5'-TGGCDapCTTTDapG-GTGGCTG-3'; SEQ ID NO:29), mismatch AS141-DAP (5'-GTGCCDapTTTGDapGTGGCTG-3'; SEQ ID NO:30), combination of ASA4-DAP and AS141-DAP (total of 100 µg) or saline in 50 µl of 0.9% NaCl intratracheally. Ten minutes later, ovalbumin challenge was performed by injecting 200 micrograms of ovalbumin in 50 µl of 0.9% saline intratracheally. After 15 hours, the rats were again intubated after general anesthesia, baseline lung resistance measured and doubling concentrations of leukotriene D4 injected intratracheally (50 ng to 1600 ng) until baseline lung resistance doubled (EC200).

Experiments Assessing the Cellular Influx into the Lungs after Antigen Challenge On day 14, the rats were intubated after general anesthesia with pentothal (65 mg/kg) and received 200 µg of ASA4, ASA4-DAP (5'-DapCTCDapTDapTTCDapTDapGGGTG-3'; SEQ ID NO:27), AS141-DAP (5'-TGGCDapCTTTDapG-GTGGCTG-3'; SEQ ID NO:29), mismatch AS141-DAP (5'-GTGCCDapTTTGDapGTGGCTG-3'; SEQ ID NO:30), combination of ASA4-DAP and AS141-DAP (total of 100 µg) or saline in 50 µl of 0.9% NaCl intratracheally. Twenty minutes later ovalbumin challenge is performed by injecting 200 µg of ovalbumin in 50 µl of 0.9% saline intratracheally. After 15 hours, the rats were again intubated after general anesthesia, and a lung lavage consisting of 5 times 5 ml instillation was performed. Cells were washed, counted and centrifuged onto slides in a Cytospin III™. A differential cell count was finally performed.

Experiments Assessing the Cellular Influx into the Lungs after Adenosine or DAP Administration Fourteen days after sensitization, the rats were intubated after anesthesia with pentothal 65 mg/kg, and 100 µg of adenosine or 2-amino-2'-deoxyadenosine or of 2-amino-2'deoxyadenosine followed 10 minutes later by adenosine or of saline was injected intratracheally in 50 µl. Fifteen hours later, the rats were intubated after general anesthesia with pentothal, and a lung lavage was performed and the cells were counted as described above.

C) RESULTS

Example 1

Figure 2A:
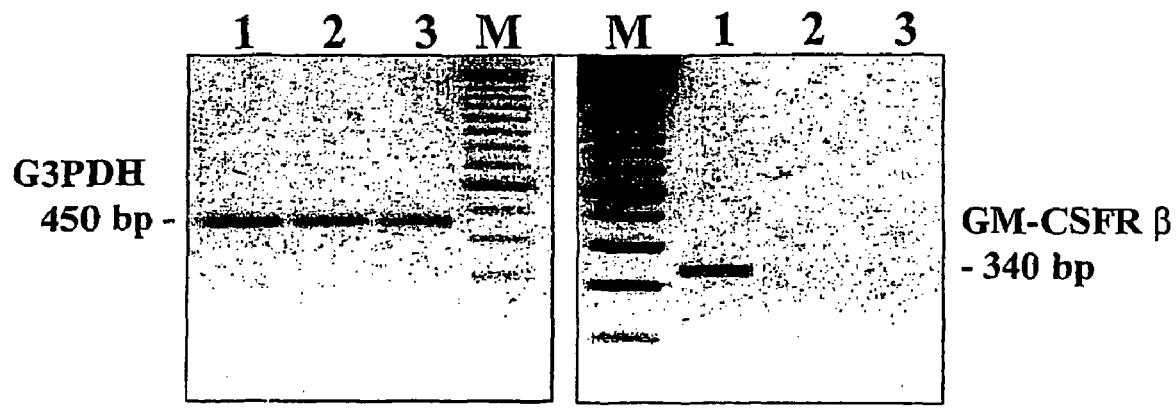
FIG. 2A are pictures of semi-quantitative PCRs showing the biological effectiveness of different antisenses to the common Beta chain of human GM-CSF, IL-3 and IL-5 receptor in U937 cells. 1=Non treated cells; 2=Cells treated with antisense AS107; 3=Cells treated with antisense AS107 containing DAP instead of 2 adenosine bases (AS107-DAP); and M=Molecular weights markers. G3PDH 450 bp=is the number of bases at which the G3PDH housekeeping gene is found; GM-CSFRβ 340 bp: is the number of bases at which the common Beta chain band is found.

Replacing Adenosine by DAP is at Least as Effective In Vitro as a Regular Phosphorothioate Antisense Oligonucleotide A first set of experiments was designed in order to determine whether replacement of adenosine by DAP affected the in vitro efficacy of AS oligonucleotides. It is to be noted in FIG. 2A that the biological effectiveness of antisense to the common Beta chain of human GM-CSF, IL-3 and IL-5 receptor is not affected by replacing adenosine by 2-amino-2'deoxyadenosine in U937 cells that express this receptor. AS107 is a 19 mer oligonucleotide that contains 2 adenosine bases. The adenosine bases were replaced by DAP (AS107-DAP). This modified oligonucleotide was at least equally effective at blocking the mRNA for the common Beta chain when assessed by semi-quantitative PCR (with G3PDH as a housekeeping gene) as AS107 containing adenosine (AS 107).

Figure 2B:
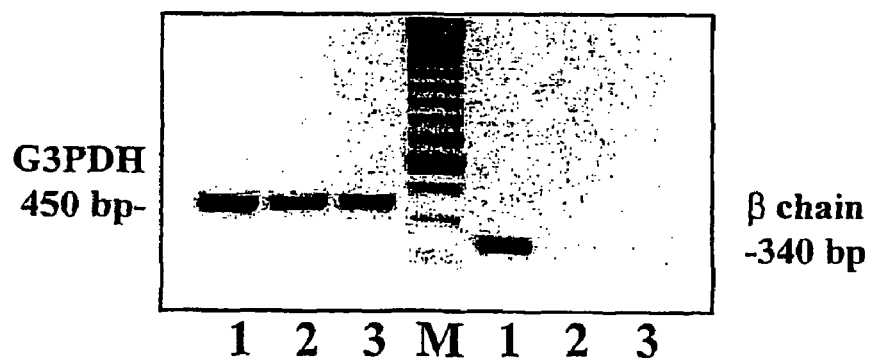
FIG. 2B is a picture of semi-quantitative PCRs showing the biological effectiveness of antisense to the common Beta chain of human GM-CSF, IL-3 and IL-5 receptor in TF-1 cells. 1=Non treated cells; 2=Cells treated with antisense AS107; 3=Cells treated with antisense AS107 containing DAP instead of 2 adenosine bases (AS107-DAP); and M=Molecular weights markers. G3PDH 450 bp is the number of bases at which the G3PDH housekeeping gene is found; β chain 340 bp is the number of bases at which the common Beta chain band is found.

To confirm the efficacy in another cell line, experiments were repeated in TF1 cells that are dependent on GM-CSF for their survival. It is to be noted in FIG. 2B that AS107-DAP to the common Beta chain of human GM-CSF, IL-3 and IL-5 receptor was at least equally effective at blocking mRNA expression as AS107 containing adenosine (AS107). Replacing adenosine by DAP in antisense oligonucleotides is effective in vitro.

Example 2

Figure 3:
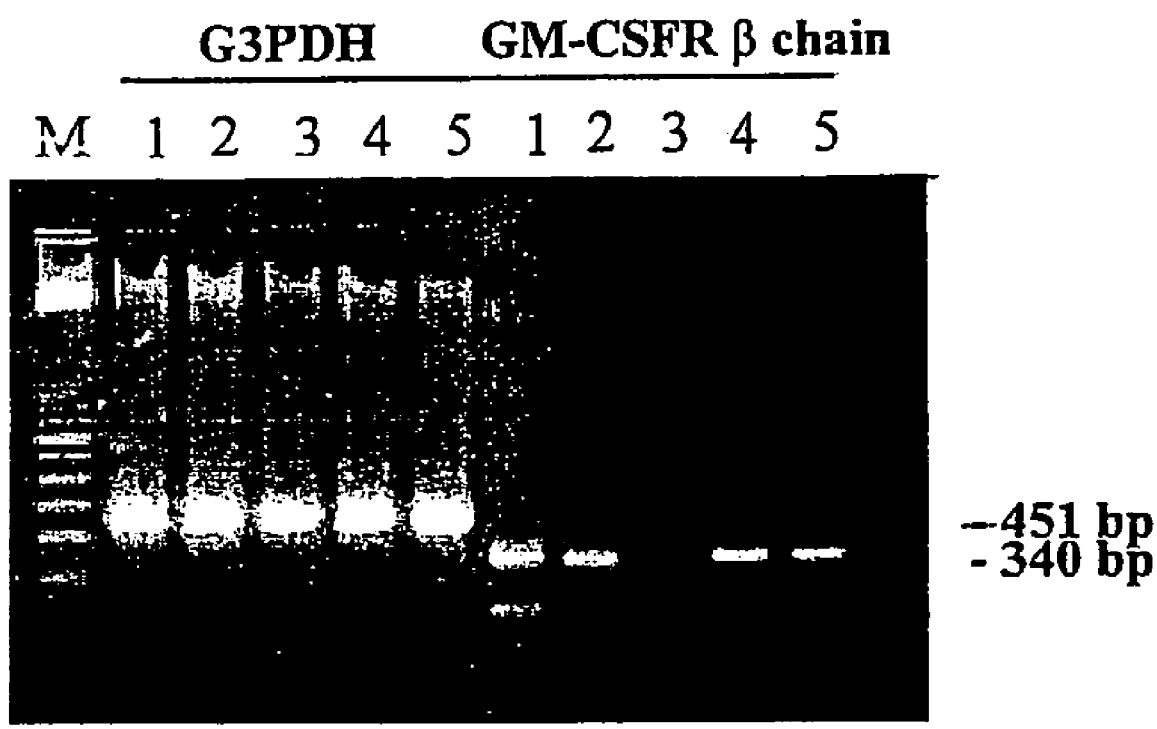
FIG. 3 is a picture of semi-quantitative PCRs showing the biological ineffectiveness in TF-1 cells of replacing adenosine by its analog inosine in the antisense to the common Beta chain of human GM-CSF, IL-3 and IL-5 receptor. 1=TF-1 Control (Non treated cells); 2=Cells treated with sense AS107; 3 Cells treated with antisense AS107; 4=Cells treated with antisense AS107 containing inosine instead of 2 adenosine bases (AS107-I); 5=Cells treated with antisense AS107 having a one base mismatch; and M=Molecular weights markers. G3PDH 450 bp is the number of bases at which the G3PDH housekeeping gene is found; β chain 340 bp is the number of bases at which the common Beta chain band is found.

Not all Substitutes of Adenosine are Effective at Inhibiting Genes when Incorporated into Phosphorothioate Antisense Oligonucleotides Experiments were performed in order to determine whether substituting adenosine would affect the efficacy of antisense oligonucleotides. It is to be noted in FIG. 3 that the effectiveness of the same antisense oligonucleotide as described above (AS107) is lost when both adenosines are replaced by inosine. Antisenses containing inosine (AS107-I) was not effective at inhibiting mRNA expression when assessed by semi-quantitative PCR and compared to AS107 containing adenosine. Experiments were performed by incubating U937 cells with medium alone, AS107 or AS107-I at a concentration of 10 μmol for six hours prior to isolating RNA and performing semi-quantitative PCR.

Example 3

An Increase in Lung Resistance Occurs after Intratracheal Injection of Phosphorothioate Antisense Oligonucleotides that is not Related to Adenosine Experiments were performed to assess the effect on lung resistance after rapid intratracheal injection of phosphorothioate antisense oligonucleotides contained in 50 μl of saline.

Figure 4A:
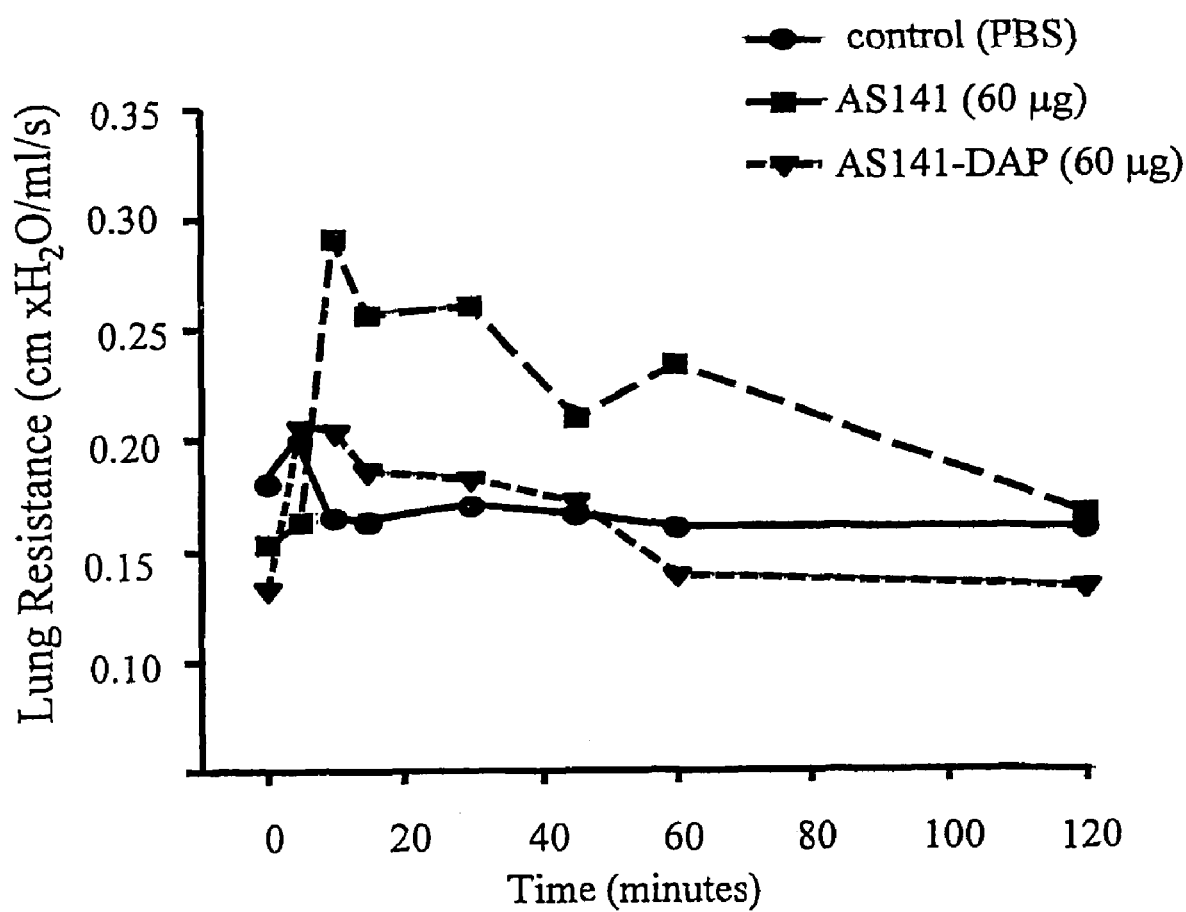
FIG. 4A is a graph showing the effects, on lung resistance of sensitized Brown Norway rats, of intratracheal administration of an antisense phosphorothioate oligonucleotide (AS141) directed against the common Beta chain of rat GM-CSF, IL-3 and IL-5, as compared to the effects of the same antisense containing DAP instead of 2 adenosine bases (AS141-DAP). Lung resistance was measured 0-2 h after administration of a dose of 60 μg of each oligonucleotide.

FIG. 4A illustrates the effects of intratracheal administration of an antisense phosphorothioate oligonucleotide directed against the common Beta chain of rat GM-CSF, IL-3 and IL-5 (AS141, a 19 mer oligonucleotide that contains 2 adenosines) and the effect of a DAP-substituted phosphorothioate antisense oligonucleotide (AS141-DAP) of the same sequence, at a dose of 60 μg each, on lung resistance of sensitized Brown Norway (BN) rats. For these experiments and the following, sensitized Brown Norway rats were employed as previously described (Renzi P M, Am Rev Respir Dis 146:163-9; 1992). The injection of phosphate buffered saline caused a mild increase in lung resistance 25% maximal increase. Regular antisense, which included less than 15% adenosine caused a moderate increase in lung resistance (87%). The DAP-modified oligonucleotides caused a mild to moderate increase (33%) in lung resistance. Nyce has suggested in WO 00/62736 and WO 00/09525 that the increase in lung resistance is caused by the adenosine that is included in the oligonucleotide. However, the oligonucleotides would not have found the time to degrade and release adenosine (a few minutes), and the antisense oligonucleotide that was employed contained only 10% adenosine (which, according to WO 00/62736 and WO 00/09525, should not have an effect on lung resistance).

Figure 4B:
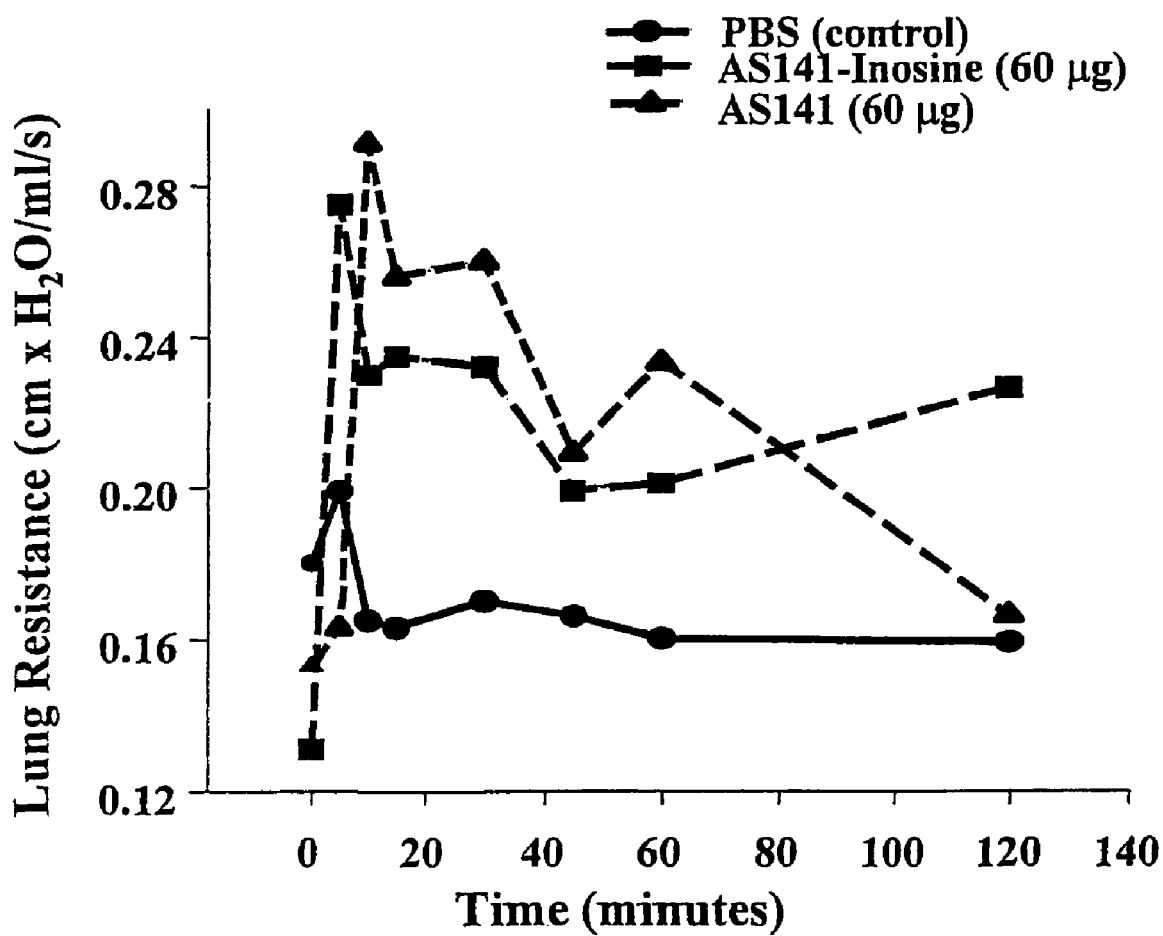
FIG. 4B is a graph showing the effects, on lung resistance of sensitized Brown Norway rats, of intratracheal administration of an antisense phosphorothioate oligonucleotide (AS141) directed against the common Beta chain of rat GM-CSF, IL-3 and IL-5, as compared to the effects of the same antisense containing inosine instead of 2 adenosine bases (AS141-Inosine). Lung resistance was measured 0-2 h after administration of a dose of 60 μg of each oligonucleotide.

An assay was performed to evaluate whether bronchospasms were due to the 2 adenosines that were replaced, in AS141, by 2 inosines since it is known that inosine does not cause bronchoconstriction of the lungs/airways compared to adenosine, (Mann, J. C. et al., J Appl Physiol 61: 1667-76, 1986). As shown in FIG. 4B, the intratracheal administration of the same antisense phosphorothioate oligonucleotide directed against the common Beta chain of rat GM-CSF, IL-3 and IL-5 (AS141) where inosine was substituted for adenosine (AS141-Inosine) also caused a temporary increase in lung resistance (by 108%). These results show that intratracheal injection of antisense oligonucleotides temporarily increases lung resistance by a mechanism that does not seem related to adenosine.

Example 4

Effect of Different DAP Analogs on Lung Resistance

Figure 5:
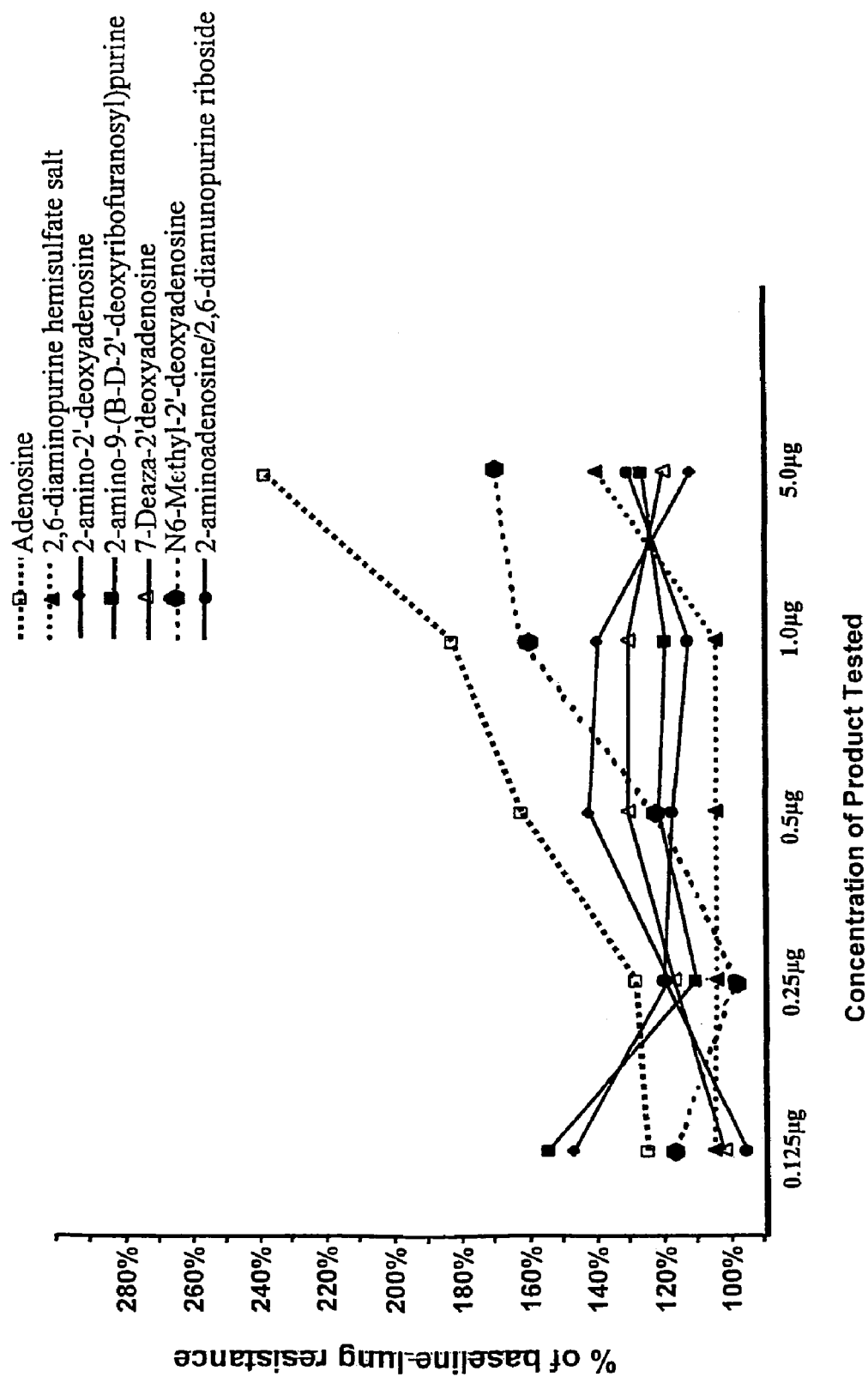
FIG. 5 is a graph showing the effects, on lung resistance of sensitized rat, of intratracheal instillation of adenosine, DAP (2-amino-2'deoxyadenosine) and analogs thereof.

We assessed the effects of intratracheal administration of DAP analogs and of adenosine on lung resistance in Brown Norway rats. As shown in FIG. 5, adenosine, DAP, and five different analogs of DAP were studied. For each compound, a minimum of six rats were studied and the average % baseline lung resistance is presented as a function of the intratracheal dose of DAP or its analogs. As can be seen in this figure, lung resistance is gradually increased to peak at a concentration of 5 μg of adenosine whereas this does not occur with 2-amino-2'deoxyadenosine (DAP) or the analogs thereof under study. These results thus show that, contrary to adenosine, DAP and its analogs does not significantly increase lung resistance. Since oligonucleotides are degraded progressively within the lungs it may be unexpectedly advantageous to use these compounds instead of adenosine.

Example 5

Figure 6A:
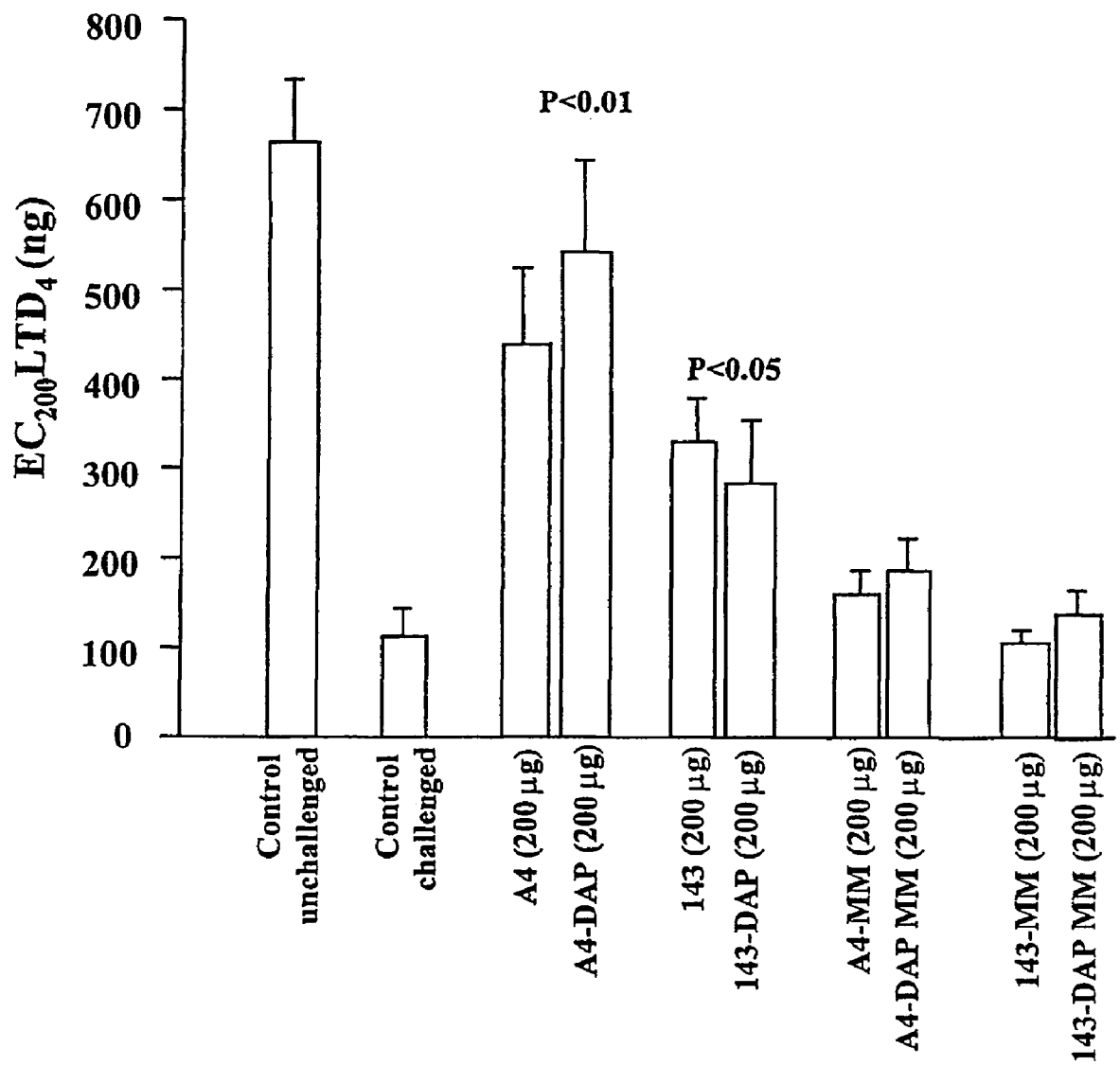
FIG. 6A is a bar graph showing that incorporation of DAP in oligonucleotides antisense to the rat CCR3 and the common β chain of IL-3/IL-5/GM-CSF receptors increases the in vivo physiological effectiveness of these antisenses. Biological activity of the antisenses were measured in the rat model of asthma: Control unchallenged; Control challenged; Rats treated with 200 μg of antisense ASA4 and AS141 (18 nucleotides); Rats treated with 200 μg of antisense ASA4 and AS141 containing DAP instead of adenosine bases (ASA4-DAP; 141-DAP); Rats treated with 200 μg of mismatch antisense ASA4 and AS141; and Rats treated with 200 μg ASA4-DAP and AS141-DAP mismatch antisense. Responsiveness to leukotriene D4 was measured 15 hours after ovalbumin challenge.
Figure 6B:
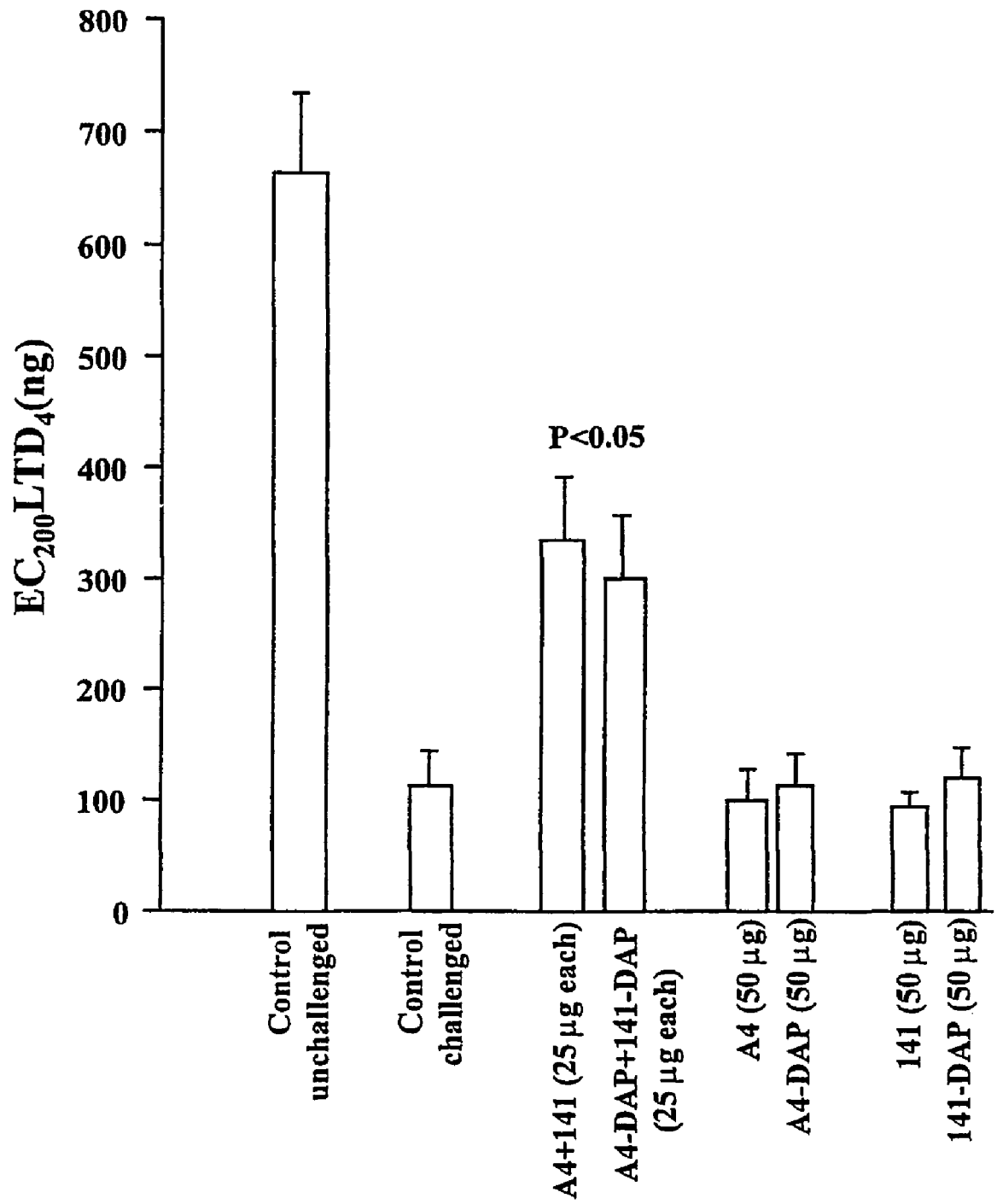
FIG. 6B, is a bar graph showing that the combination of two regular and two DAP containing oligonucleotides (total 50 μg) is more effective than 50 μg of each oligonucleotide alone.

DAP-Modified Phosphorothioate Antisense Oligonucleotides are Effective at Inhibiting the Airway Hyper-Responsiveness That Occurs After Antigen Challenge In Vivo The in vivo biological activity of DAP-modified antisense directed against the rat CCR3 and the common β chain of IL-3/IL-5/GM-CSF receptors in the rat model of asthma is demonstrated in FIG. 6A. ASA4 is an 18 mer phosphorothioate antisense oligonucleotide that has been shown to inhibit the CCR3 receptor and inhibit the eosinophil influx that occurs after antigen challenge (see WO 99/66037). AS141 is also an 18 mer phosphorothioate antisense oligonucleotide that has been shown to inhibit the common β chain of IL-3/IL-5/GM-CSF receptors and inhibit the eosinophil influx that occurs after antigen challenge (see WO 99/66037) ASA4 contains 5 adenosine bases (28% adenosine). AS143 contains 2 adenosine bases. It is to be noted that ASA4-DAP significantly decreased airway responsiveness to leukotriene D4 15 hours after ovalbumin challenge when compared to rats that received no AS (control challenged; p<0.01) or DAP mismatch treated rats. It is also to be noted that ASA4-DAP tended to be more effective than unmodified ASA4 and was no different than results obtained from unchallenged rats. AS141 also decreased significantly the hyperresponsiveness to $LTD_4$ (P<0.05) when compared to control challenged and 141-DAP mismatch treated rats. Moreover, airway responsiveness to $LTD_4$ was significantly decreased in the rats treated with the combination of CCR3 and the common β chain oligonucleotides compared to each antisense oligonucleotide and this combination was as effective as the combination of DAP oligonucleotides (total 50 μg; FIG. 6B).

Example 6

Figure 7A:
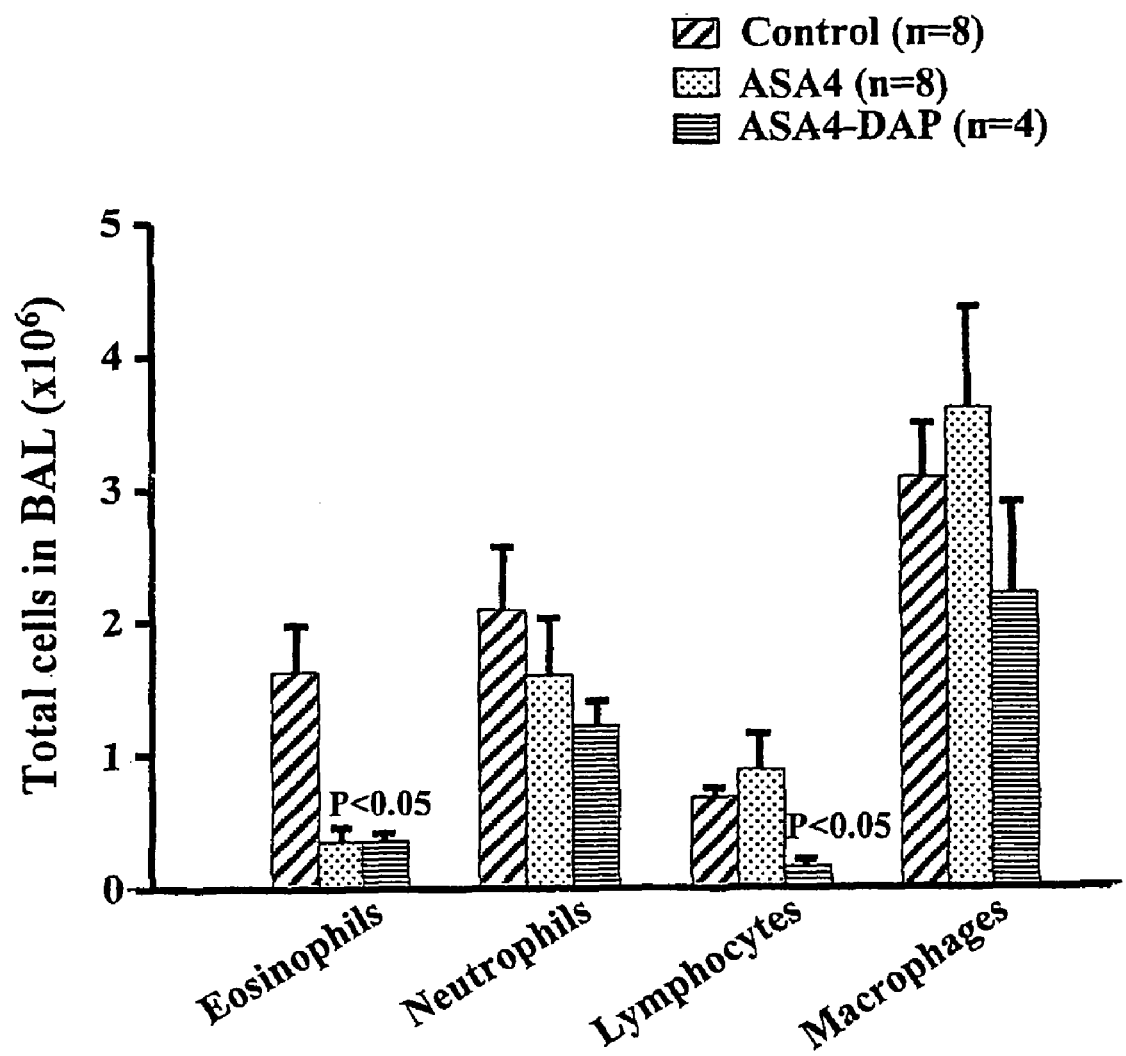
FIG. 7A, is a bar graph showing that oligonucleotides against CCR3 containing DAP are more effective at inhibiting lung inflammation in vivo after antigen challenge than oligonucleotides without DAP.
Figure 7B:
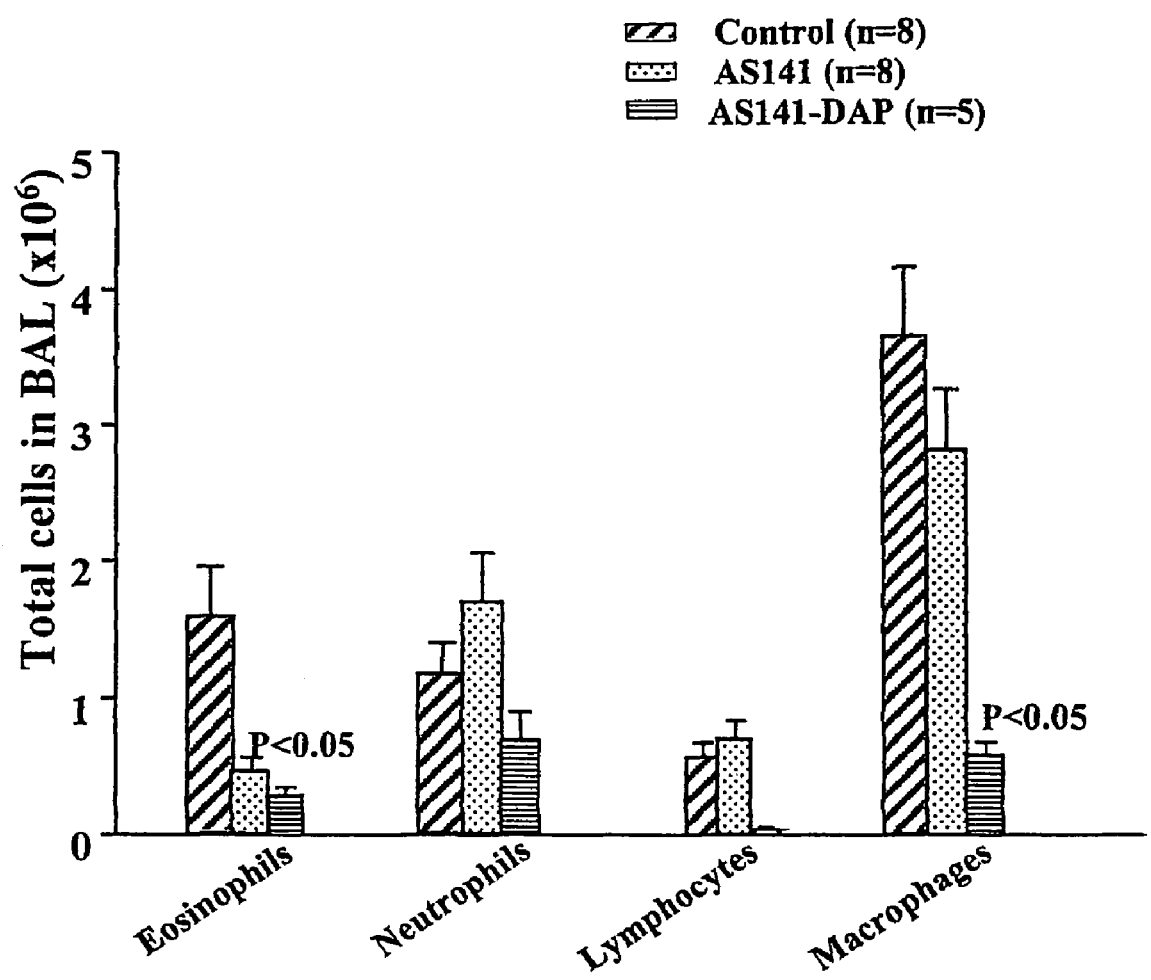
FIG. 7B, is a bar graph showing that oligonucleotides against the common β chain of IL-3/IL-5/GM-CSF receptors containing DAP are more effective at inhibiting lung inflammation in vivo after antigen challenge than oligonucleotides without DAP.
Figure 7C:
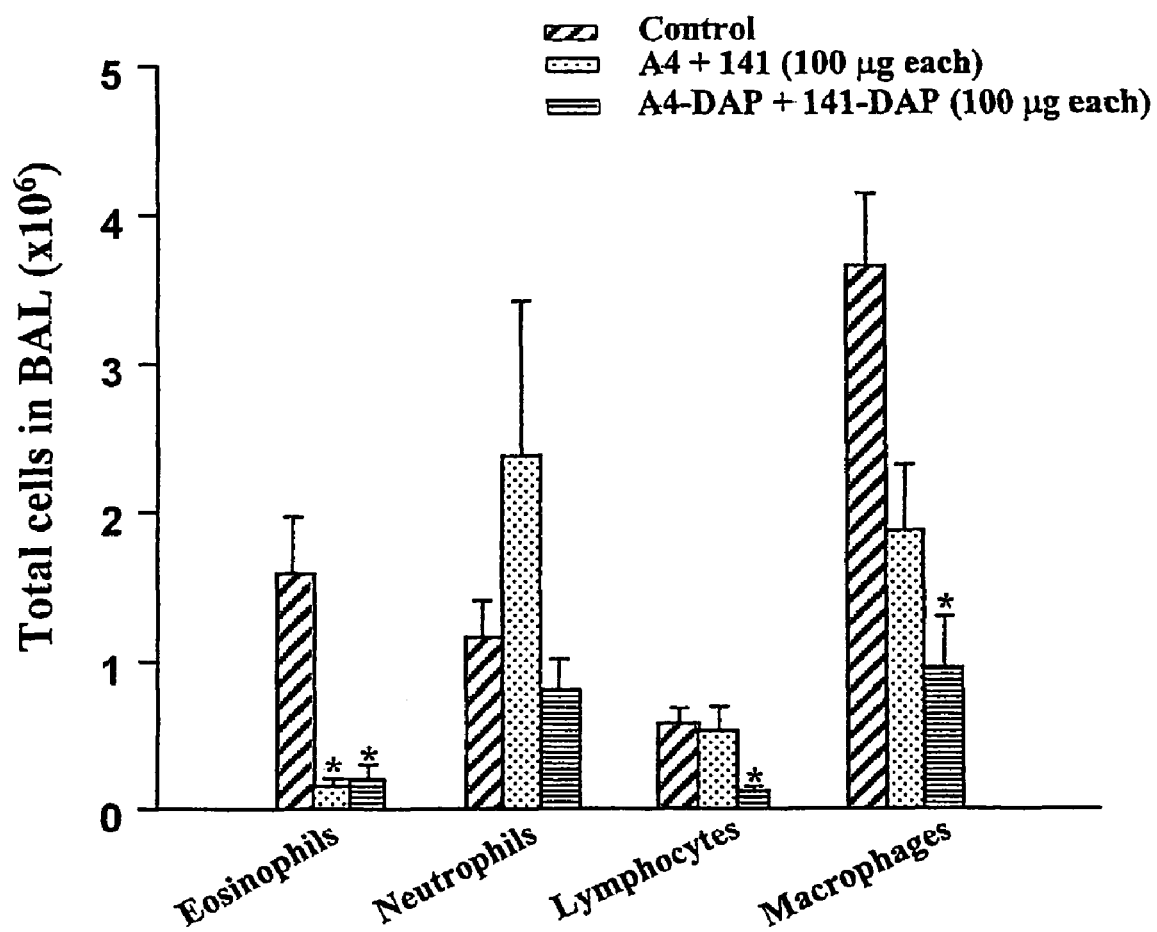
FIG. 7C, is a bar graph showing that the combination of two DAP containing oligonucleotides (total 50 μg) is more effective at inhibiting lung inflammation in vivo after antigen challenge than the combination of two regular oligonucleotides without DAP.

DAP-Modified Phosphorothioate Antisense Oligonucleotides are More Effective Than Conventional Antisense Oligonucleotides at Inhibiting the Airway Inflammation that Occurs after Antigen Challenge In Vivo These experiments were performed with antisense oligonucleotides directed against the rat CCR3 receptor or the common Beta chain of IL-3, 5 and GM-CSF. Ovalbumin sensitized and challenged rats were treated by intratracheal injection of saline, 200 μg of regular ASA4 or 200 μg of ASA4-DAP ten minutes prior to ovalbumin challenge. After 15 hours, the rats were anesthetized intubated and bronchoalveolar lavage was performed for total cell count and differential. The results show that administration of both regular ASA4 (FIG. 7A) and AS141 (FIG. 7B) and both ASA4-DAP and AS141-DAP effectively inhibited the recruitment of eosinophils (by 84% and 83% respectively; FIG. 7A). However AS4DAP tended to decrease neutrophil and macrophage recruitment and significantly decreased lymphocyte recruitment (by 74%). 141-DAP significantly decreased macrophage recruitment (p<0.05) as well. The combination of two A4-DAP and 141-DAP oligonucleotides (total 200 μg) also significantly decreased the recruitment of lymphocytes and macrophages (FIG. 7C). These results show that DAP-modified oligonucleotides are not only effective but also have a broader anti-inflammatory effect than regular oligonucleotides.

Example 7

Adenosine has Pro-Inflammatory Effects in the Lungs that are Specific for Eosinophil Recruitment and DAP is an Antagonist of the Adenosine Pro-Inflammatory Effects In another experiment, groups of six sensitized but unchallenged Brown Norway rats were anesthetized with pentothal and endotracheally intubated. The rats then received an intratracheal injection of either (1) saline (control), (2) 100 μg of adenosine, (3) 100 μg of 2-amino-2'-deoxyadenosine (DAP) or (4) 100 μg of DAP followed by 100 μg of adenosine 10 minutes later. The rats were awakened, re-anesthetized and intubated 15 hours later for a lung lavage. Cells that were present in media collected from the lavage, were counted and a differential was obtained on Cytospin∩ slides.

Figure 8:
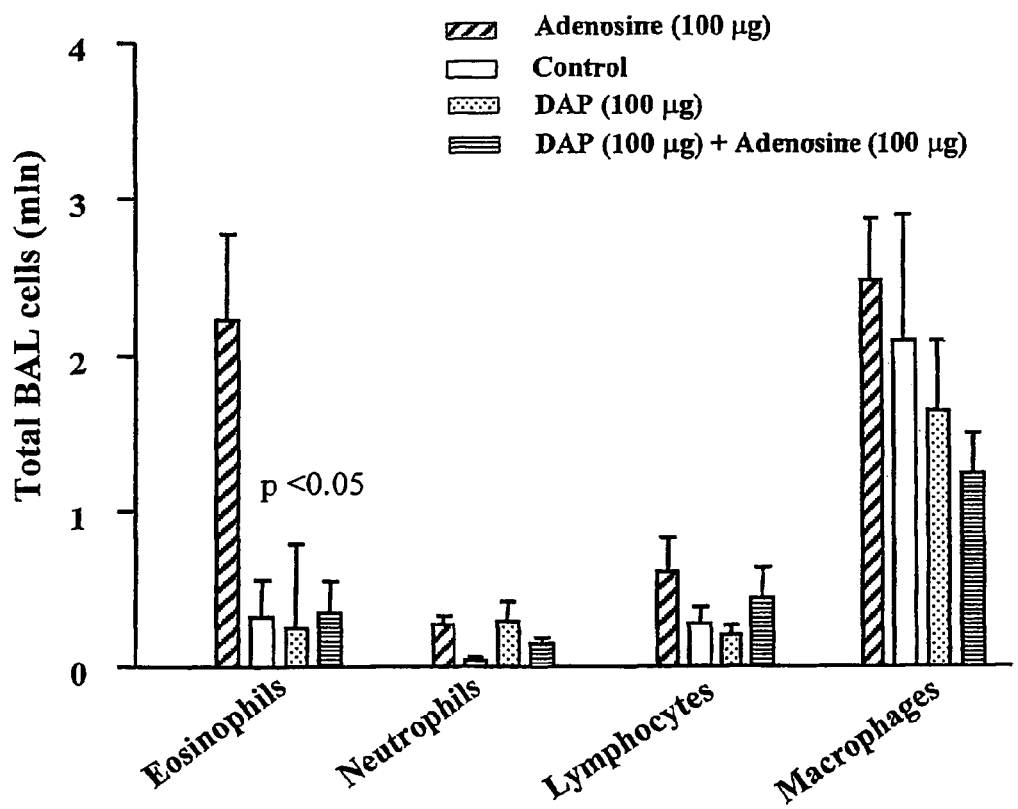
FIG. 8 is a bar graph showing that adenosine selectively increases eosinophil recruitment into the lungs of rats whereas DAP does not, and that DAP is an antagonist of the pro-inflammatory effects of adenosine.

As shown in FIG. 8, adenosine is pro-inflammatory in the lungs, leading to a selective recruitment of eosinophils (more than 10 fold increase), without significantly affecting other cell types. To the opposite, DAP does not increase the cellularity of lung lavage and completely inhibits the recruitment of eosinophils that is induced by adenosine.

D) CONCLUSIONS

In view of the above, DAP-substituted antisense oligonucleotides have the following advantages when compared to unmodified antisenses or inosine-modified antisenses:

a) As shown in FIGS. 1 to 8 and documented in the present patent application, the chemical structure and properties of DAP and DAP analogs are different from adenosine. These different chemistries cause antisense oligonucleotides containing DAP and/or DAP analogs to have different chemistries, hybridization properties and stability as compared to unmodified antisenses.

b) Example 1 shows how DAP phosphorothioate antisenses are effective in different cell lines in vitro.

c) Example 2 shows that not all substitutes of adenosine are effective at inhibiting genes when incorporated into phosphorothioate antisense oligonucleotides (as shown with inosine).

d) Example 3 shows that an increase in lung resistance occurs after intratracheal injection of phosphorothioate antisense oligonucleotides, and that this increase is not related to adenosine. Indeed, even though inosine does not stimulate adenosine receptors an increase in lung resistance was seen with inosine oligos. However, this increase was less important with DAP-modified oligos.

e) Example 4 shows that, although different substitutes of adenosine, DAP and analogs of DAP have different effects on lung resistance when injected intratracheally in vivo, these compounds were all much less toxic than adenosine. For instance, as shown at FIG. 5, at peak adenosine toxicity (5 μg), the relative ranking of the compounds tested was adenosine>N6-Methyl-2'deoxyadenosine>rest including DAP. However at 5 fold lower concentration (1 μg) the toxicity ranking was different with adenosine>2 amino-2 deoxyadenosine/DAP>rest. Free DAP base was used as a structure control to determine whether the sugar was required for toxicity.

f) Example 5 shows that DAP-modified phosphorothioate antisense oligonucleotides are effective at inhibiting the airway hyper-responsiveness to leukotriene D4 that occurs after antigen challenge in vivo and tend to be more effective than conventional PS oligonucleotides. The combination of two DAP-modified oligonucleotides is more effective than each oligonucleotide alone, confirming synergy.

g) Example 6 shows that DAP-modified phosphorothioate antisense oligonucleotides are more effective than conventional antisense oligonucleotides at inhibiting the airway inflammation that occurs after antigen challenge in vivo. For ASA4 there were strong trends for decreases in neutrophils and macrophages and also a significant decrease in lymphocytes, whereas these effects were not encountered with conventional PS antisense oligonucleotides. For AS141 there were strong trends for decreases in neutrophils and also a significant decrease in lymphocytes and macrophages, whereas these effects were not encountered with conventional PS antisense oligonucleotides. For the combination of ASA4 and AS141 there were strong trends for decreases in neutrophils and also a significant decrease in lymphocytes and macrophages, whereas these effects were not encountered with conventional PS antisense oligonucleotides.

h) Example 7 shows that adenosine has a pro-inflammatory effect in the lungs of rats, selectively recruiting eosinophils and that it does not have a significant effect on lymphocytes. At the same time, Example 7 shows that DAP blocks eosinophil influx, a demonstration that DAP per se is an antagonist of adenosine.

The above 7 examples show that DAP-substituted antisenses and antisenses with analogs of DAP, are inherently more effective and much less toxic for the lungs/airways than free adenosine nucleoside or unmodified antisense compounds containing adenosine.

Also, contrary to what has been suggested in WO 00/09525 and WO 00/62736, adenosines contained within the antisenses are not pro-inflammatory since antisenses with up to 28% adenosine bases were capable to inhibit eosinophil influx as much as antisenses containing no adenosine but DAP (see FIG. 7). However, since the oligonucleotides containing DAP also inhibited lymphocyte and macrophage influx (FIG. 7), and adenosine does not affect lymphocyte influx (FIG. 8), it seems that DAP contained in antisenses does exert its effects through a mechanism that is not related to the adenosine receptor(s).

In summary, DAP-antisenses thus provide an improved technology platform for the development of antisenses therapeutics and vaccines for the treatment and prevention of respiratory diseases such as asthma, allergic rhinits, chronic obstructive disease, eosinophilic cough, pulmonary fibrosis, cystic fibrosis, pathogen infections, genetic diseases and lung cancer, and any other disease where inflammation is a concern. Also, DAP per se and analogs thereof have a strong potential in anti-inflammatory drugs for inhibiting inflammation in mammals.

While several embodiments of the invention have been described, it will be understood that the present invention is capable of further modifications, and the present patent application is intended to cover any variations, uses, or adaptations of the invention, following in general the principles of the invention and including such departures from the present disclosure as to come within knowledge or customary practice in the art to which the invention pertains.

The invention claimed is:

1. A method for increasing in vivo anti-inflammatory efficacy of an oligonucleotide comprising:
   a. identifying an oligonucleotide to be administered to the respiratory system for decreasing inflammation therein in a mammal in need thereof, the oligonucleotide having at least one adenosine nucleotide, and
   b. replacing the at least one adenosine nucleotide with a nucleotide substitute selected from the group consisting of 2-amino-2'-deoxyadenosine and salts thereof.

2. The method of claim 1, wherein said nucleotide substitute is 2-amino-2'-deoxyadenosine.

3. The method of claim 1, wherein the oligonucleotide is an antisense oligonucleotide.

4. The method of claim 1, wherein the inflammation is associated with one or more respiratory system diseases.

5. The method of claim 4, wherein the respiratory system disease is a sickness associated with an inflammation of the lungs, the airways and/or the nose.

6. The method of claim 4, wherein the respiratory system disease is selected from the group consisting of pulmonary fibrosis, adult respiratory distress syndrome, cystic fibrosis, chronic obstructive lung disease, chronic bronchitis, eosinophilic bronchitis, asthma, allergy, allergic rhinitis, sinusitis and hypereosinophilia.

7. The method of claim 1, wherein the oligonucleotide is SEQ ID NO: 8.

8. The method of claim 1, wherein the oligonucleotide has at least one mononucleotide linking residue selected from the group consisting of: methylphosphonate, phosphotriester, phosphorothioate, phosphodiester, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methylmino), methyleneoxy (methylimino), and phosphoramidate residues.

9. The method of claim 1, wherein the resulting oligonucleotide decreases or inhibits airway hyper-responsiveness.

10. The method of claim 1, wherein the oligonucleotide is for administration to the lung.

* * * * *

```
                              SEQUENCE LISTING

<160> NUMBER OF SEQ ID NOS: 30

<210> SEQ ID NO 1
<211> LENGTH: 20
<212> TYPE: DNA
<213> ORGANISM: Artificial sequence
<220> FEATURE:
<223> OTHER INFORMATION: Sequence is completely synthesized

<400> SEQUENCE: 1
agaccttcat gttcccagag                                                   20

<210> SEQ ID NO 2
<211> LENGTH: 20
<212> TYPE: DNA
<213> ORGANISM: Artificial sequence
<220> FEATURE:
<223> OTHER INFORMATION: Sequence is completely synthesized

<400> SEQUENCE: 2
gttcccagag cttgccacct                                                   20

<210> SEQ ID NO 3
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 3
cctgcaagac cttcatgtt                                                    19

<210> SEQ ID NO 4
<211> LENGTH: 20
<212> TYPE: DNA
<213> ORGANISM: Artificial sequence
<220> FEATURE:
<223> OTHER INFORMATION: Sequence is completely synthesized

<400> SEQUENCE: 4
cgcccacagc ccgcagagcc                                                   20

<210> SEQ ID NO 5
<211> LENGTH: 20
<212> TYPE: DNA
<213> ORGANISM: Artificial sequence
<220> FEATURE:
<223> OTHER INFORMATION: Sequence is completely synthesized

<400> SEQUENCE: 5
ctccatgcag cctctcgcct                                                   20

<210> SEQ ID NO 6
<211> LENGTH: 20
<212> TYPE: DNA
<213> ORGANISM: Artificial sequence
```

```
<220> FEATURE:
<223> OTHER INFORMATION: Sequence is completely synthesized

<400> SEQUENCE: 6
ccgccggcgc agagcagcag                                                  20

<210> SEQ ID NO 7
<211> LENGTH: 20
<212> TYPE: DNA
<213> ORGANISM: Artificial sequence
<220> FEATURE:
<223> OTHER INFORMATION: Sequence is completely synthesized

<400> SEQUENCE: 7
cgcccccgcc cccgcccccg                                                  20

<210> SEQ ID NO 8
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 8
gggtctgcag cgggatggt                                                   19

<210> SEQ ID NO 9
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 9
ggtctgcagc gggatggtt                                                   19

<210> SEQ ID NO 10
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 10
agggtctgca gcgggatgg                                                   19

<210> SEQ ID NO 11
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 11
gcagggtctg cagcgggat                                                   19

<210> SEQ ID NO 12
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 12
gcagcgggat ggtttcttc                                                   19
```

```
<210> SEQ ID NO 13
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 13
cagcgggatg gtttcttct                                               19

<210> SEQ ID NO 14
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 14
gtctgcagcg ggatggttt                                               19

<210> SEQ ID NO 15
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 15
ctgggccatc agtgctctg                                               19

<210> SEQ ID NO 16
<211> LENGTH: 17
<212> TYPE: DNA
<213> ORGANISM: Artificial sequence
<220> FEATURE:
<223> OTHER INFORMATION: Sequence is completely synthesized

<400> SEQUENCE: 16
ccctgacata gtggatc                                                 17

<210> SEQ ID NO 17
<211> LENGTH: 16
<212> TYPE: DNA
<213> ORGANISM: Artificial sequence
<220> FEATURE:
<223> OTHER INFORMATION: Sequence is completely synthesized

<400> SEQUENCE: 17
tagcatggca ctgggc                                                  16

<210> SEQ ID NO 18
<211> LENGTH: 19
<212> TYPE: DNA
<213> ORGANISM: artificial sequence
<220> FEATURE:
<223> OTHER INFORMATION: Sequence is completely synthesized

<400> SEQUENCE: 18
ggagccagtc ctagcgagc                                               19

<210> SEQ ID NO 19
<211> LENGTH: 19
<212> TYPE: DNA
<213> ORGANISM: Artificial sequence
<220> FEATURE:
<223> OTHER INFORMATION: Sequence is completely synthesized
```

```
<400> SEQUENCE: 19
accatcccgc tgcagaccc                                                    19

<210> SEQ ID NO 20
<211> LENGTH: 19
<212> TYPE: DNA
<213> ORGANISM: Artificial sequence
<220> FEATURE:
<223> OTHER INFORMATION: Sequence is completely synthesized

<400> SEQUENCE: 20
gggtctgcag cgggatggt                                                    19

<210> SEQ ID NO 21
<211> LENGTH: 19
<212> TYPE: DNA
<213> ORGANISM: Artificial sequence
<220> FEATURE:
<223> OTHER INFORMATION: Sequence is completely synthesized
<220> FEATURE:
<221> NAME/KEY: misc_feature
<222> LOCATION: (9)..(9)
<223> OTHER INFORMATION: "n" corresponds to 2,6-diaminopurine nucleoside
      (DAP)
<220> FEATURE:
<221> NAME/KEY: misc_feature
<222> LOCATION: (15)..(15)
<223> OTHER INFORMATION: "n" corresponds to 2,6-diaminopurine nucleoside
      (DAP)

<400> SEQUENCE: 21
gggtctgcng cgggntggt                                                    19

<210> SEQ ID NO 22
<211> LENGTH: 19
<212> TYPE: DNA
<213> ORGANISM: Artificial sequence
<220> FEATURE:
<223> OTHER INFORMATION: Sequence is completely synthesized
<220> FEATURE:
<221> NAME/KEY: misc_feature
<222> LOCATION: (9)..(9)
<223> OTHER INFORMATION: "n" corresponds to an Inosine
<220> FEATURE:
<221> NAME/KEY: misc_feature
<222> LOCATION: (15)..(15)
<223> OTHER INFORMATION: "n" corresponds to an Inosine

<400> SEQUENCE: 22
gggtctgcng cgggntggt                                                    19

<210> SEQ ID NO 23
<211> LENGTH: 18
<212> TYPE: DNA
<213> ORGANISM: Artificial sequence
<220> FEATURE:
<223> OTHER INFORMATION: Sequence is completely synthesized

<400> SEQUENCE: 23
tggcacttta ggtggctg                                                     18

<210> SEQ ID NO 24
<211> LENGTH: 18
<212> TYPE: DNA
<213> ORGANISM: Artificial sequence
<220> FEATURE:
<223> OTHER INFORMATION: Sequence is completely synthesized
```

```
<220> FEATURE:
<221> NAME/KEY: misc_feature
<222> LOCATION: (5)..(5)
<223> OTHER INFORMATION: "n" corresponds to 2,6-diaminopurine nucleoside
      (DAP)
<220> FEATURE:
<221> NAME/KEY: misc_feature
<222> LOCATION: (10)..(10)
<223> OTHER INFORMATION: "n" corresponds to 2,6-diaminopurine nucleoside
      (DAP)

<400> SEQUENCE: 24 tggcncttttn ggtggctg                                                     18

<210> SEQ ID NO 25
<211> LENGTH: 18
<212> TYPE: DNA
<213> ORGANISM: Artificial sequence
<220> FEATURE:
<223> OTHER INFORMATION: Sequence is completely synthesized
<220> FEATURE:
<221> NAME/KEY: misc_feature
<222> LOCATION: (5)..(5)
<223> OTHER INFORMATION: "n" corresponds to an Inosine
<220> FEATURE:
<221> NAME/KEY: misc_feature
<222> LOCATION: (10)..(10)
<223> OTHER INFORMATION: "n" corresponds to an Inosine

<400> SEQUENCE: 25 tggcncttttn ggtggctg                                                     18

<210> SEQ ID NO 26
<211> LENGTH: 18
<212> TYPE: DNA
<213> ORGANISM: Artificial sequence
<220> FEATURE:
<223> OTHER INFORMATION: Sequence is completely synthesized

<400> SEQUENCE: 26
actcatattc atagggtg                                                      18

<210> SEQ ID NO 27
<211> LENGTH: 18
<212> TYPE: DNA
<213> ORGANISM: Artificial sequence
<220> FEATURE:
<223> OTHER INFORMATION: Sequence is completely synthesized
<220> FEATURE:
<221> NAME/KEY: misc_feature
<222> LOCATION: (1)..(1)
<223> OTHER INFORMATION: "n" corresponds to 2,6-diaminopurine nucleoside
      (DAP)
<220> FEATURE:
<221> NAME/KEY: misc_feature
<222> LOCATION: (5)..(5)
<223> OTHER INFORMATION: "n" corresponds to 2,6-diaminopurine nucleoside
      (DAP)
<220> FEATURE:
<221> NAME/KEY: misc_feature
<222> LOCATION: (7)..(7)
<223> OTHER INFORMATION: "n" corresponds to 2,6-diaminopurine nucleoside
      (DAP)
<220> FEATURE:
<221> NAME/KEY: misc_feature
<222> LOCATION: (11)..(11)
<223> OTHER INFORMATION: "n" corresponds to 2,6-diaminopurine nucleoside
      (DAP)
<220> FEATURE:
<221> NAME/KEY: misc_feature
<222> LOCATION: (13)..(13)
<223> OTHER INFORMATION: "n" corresponds to 2,6-diaminopurine nucleoside
      (DAP)
```

<400> SEQUENCE: 27
nctcntnttc ntngggtg                                         18

<210> SEQ ID NO 28
<211> LENGTH: 18
<212> TYPE: DNA
<213> ORGANISM: Artificial sequence
<220> FEATURE:
<223> OTHER INFORMATION: Sequence is completely synthesized
<220> FEATURE:
<221> NAME/KEY: misc_feature
<222> LOCATION: (2)..(2)
<223> OTHER INFORMATION: "n" corresponds to 2,6-diaminopurine nucleoside
      (DAP)
<220> FEATURE:
<221> NAME/KEY: misc_feature
<222> LOCATION: (5)..(5)
<223> OTHER INFORMATION: "n" corresponds to 2,6-diaminopurine nucleoside
      (DAP)
<220> FEATURE:
<221> NAME/KEY: misc_feature
<222> LOCATION: (8)..(8)
<223> OTHER INFORMATION: "n" corresponds to 2,6-diaminopurine nucleoside
      (DAP)
<220> FEATURE:
<221> NAME/KEY: misc_feature
<222> LOCATION: (14)..(14)
<223> OTHER INFORMATION: "n" corresponds to 2,6-diaminopurine nucleoside
      (DAP)

<400> SEQUENCE: 28
cntcnttntc atgnggtg                                         18

<210> SEQ ID NO 29
<211> LENGTH: 18
<212> TYPE: DNA
<213> ORGANISM: Artificial sequence
<220> FEATURE:
<223> OTHER INFORMATION: Sequence is completely synthesized
<220> FEATURE:
<221> NAME/KEY: misc_feature
<222> LOCATION: (5)..(5)
<223> OTHER INFORMATION: "n" corresponds to 2,6-diaminopurine nucleoside
      (DAP)
<220> FEATURE:
<221> NAME/KEY: misc_feature
<222> LOCATION: (10)..(10)
<223> OTHER INFORMATION: "n" corresponds to 2,6-diaminopurine nucleoside
      (DAP)

<400> SEQUENCE: 29
tggcnctttn ggtggctg                                         18

<210> SEQ ID NO 30
<211> LENGTH: 18
<212> TYPE: DNA
<213> ORGANISM: Artificial sequence
<220> FEATURE:
<223> OTHER INFORMATION: Sequence is completely synthesized
<220> FEATURE:
<221> NAME/KEY: misc_feature
<222> LOCATION: (6)..(6)
<223> OTHER INFORMATION: "n" corresponds to 2,6-diaminopurine nucleoside
      (DAP)
<220> FEATURE:
<221> NAME/KEY: misc_feature
<222> LOCATION: (11)..(11)
<223> OTHER INFORMATION: "n" corresponds to 2,6-diaminopurine nucleoside
      (DAP)

```
<400> SEQUENCE: 30
gtgccntttg ngtggctg                                              18
```